United States Patent [19]

Hirata et al.

[11] Patent Number: 5,260,444
[45] Date of Patent: * Nov. 9, 1993

[54] DIHYDROPYRIDINE DERIVATIVE

[75] Inventors: Terukage Hirata; Yasushi Yoshimura; Masanori Kakimoto; Koichi Tamura; Harunobu Amagase, all of Hiroshima, Japan

[73] Assignee: Wakunaga Seiyaku Kabushiki Kaisha, Osaka, Japan

[*] Notice: The portion of the term of this patent subsequent to May 4, 2010 has been disclaimed.

[21] Appl. No.: 977,173

[22] Filed: Nov. 16, 1992

Related U.S. Application Data

[63] Continuation of Ser. No. 696,704, May 7, 1991, Pat. No. 5,208,245.

Foreign Application Priority Data

May 7, 1990 [JP] Japan .................. 2-117129

[51] Int. Cl.$^5$ .......................... C07D 405/12
[52] U.S. Cl. .................................. 546/269
[58] Field of Search ............... 546/269; 514/337

[56] References Cited

U.S. PATENT DOCUMENTS 4,532,248  7/1985  Franckowiak et al. ............. 546/116

OTHER PUBLICATIONS

Merck Index pp. 1047–1048.
Burger Medicinal Chemistry 2nd Edition pp. 565–601.
Thomas Jour. of Cardiovascular Pharmac. 6:1170–1176.

*Primary Examiner*—Jane T. Fan
*Attorney, Agent, or Firm*—Oblon, Spivak, McClelland, Maier & Neustadt

[57] ABSTRACT

The present invention provides dihydropyridine derivatives represented by the following formula (I)

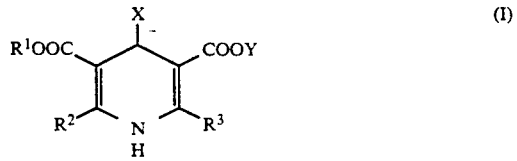

and salts thereof. They have extremely strong, slow and long-acting vasodilating action and antihypertensive action with less adverse effects so that they are useful as therapeutic agents for cardiovascular diseases.

3 Claims, No Drawings

DIHYDROPYRIDINE DERIVATIVE

This is a continuation of application Ser. No. 07/696,704, filed on May 7, 1991 now U.S. Pat. No. 5,208,245, issued May 4, 1993.

BACKGROUND OF THE INVENTION

1) Field of the Invention

The present invention relates to a novel dihydropyridine derivative or a salt thereof and a pharmaceutical agent containing the same as an effective component thereof.

2) Description of the Background Art

So far a great number of compounds with strong calcium antagonism have been discovered in dihydropyridine derivatives. Among them, nifedipine, nicardipine, nimodipine and the like have been widely used as therapeutic agents for cardiovascular diseases, such as vasodilators and antihypertensives.

However, these conventional dihydropyridine derivatives have a number of problems including a high incidence of adverse effects and insufficient duration of the action thereof, so the derivatives have not been satisfactory.

Hence, expectation has been oriented toward a novel dihydropyridine derivative with excellent pharmaceutical actions and a high degree of safety, and a therapeutic agent for cardiovascular diseases containing the same as an effective component.

In such circumstances, the present inventors have carried out investigations intensively, and have found that the derivatives represented by formula (I) into which a dihydrobenzopyranyl group is introduced as the ester side chain of the dihydropyridine skeleton thereof have extremely strong, slow and prolonged vasodilating action, antihypertensive action and the like, and that the derivatives are useful as a pharmaceutical agent. The present invention was achieved based on the above findings.

SUMMARY OF THE INVENTION

An object of the present invention is to provide a dihydropyridine derivative represented by the following formula

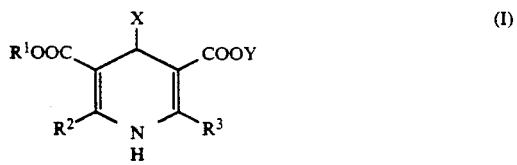

wherein $R^1$ represents a lower alkyl group which may or may not have a substituent group, a lower cycloalkyl group which may or may not have a substituent group, a lower alkenyl group which may or may not have a substituent group, a lower alkynyl group which may or may not have a substituent group, or 3,4-dihydro-2H-benzo[b]pyran-4-yl group which may or may not have a substituent group; $R^2$ and $R^3$, which may or may not be the same, independently represent a lower alkyl group which may or may not have a substituent group, amino group or a cyano group; X represents an aryl group which may or may not have a substituent group, or an unsaturated heterocyclic group which may or may not have a substituent group; and Y represents a 3,4-dihydro-2H-benzo[b]pyran-4-yl group which may or may not have a substituent group; or a salt thereof, as well as a therapeutic agent for cardiovascular diseases containing the same as an effective component thereof.

The above and other objects, features and advantages of the present invention will become apparent from the following description.

DETAILED DESCRIPTION OF THE INVENTION AND PREFERRED EMBODIMENTS

In the present invention, the term "lower" used in the description of each substituent group of the formula (I) represents a group having 1 to 7, preferably, 1 to 4 carbon atoms when the substituent group is a straight or branched group, while the term represents a group having 3 to 7 carbon atoms when the substituent group is a cyclic group.

Among all represented by $R^1$, as the lower alkyl group which may or may not have a substituent group, there can be mentioned methyl group, ethyl group, n-propyl group, isopropyl group, n-butyl group, isobutyl group, sec-butyl group, t-butyl group, pentyl group, neopentyl group, hexyl group and the like; as the lower cycloalkyl group which may or may not have a substituent group, there can be mentioned cyclopropyl group, cyclobutyl group, cyclopentyl group, cyclohexyl group and the like; as the lower alkenyl group which may or may not have a substituent group, there can be mentioned vinyl group, allyl group, butenyl group, pentenyl group, and the like; as the lower alkynyl group which may or may not have a substituent group, there can be mentioned propargyl group, butynyl group and the like. These groups may or may not be substituted with one to three groups selected from the group consisting of halogen atom (for example, fluorine atom, chlorine atom and the like), cyano group, lower alkoxy group (for example, methoxy group, ethoxy group and the like), aryloxy group (for example, phenoxy group and the like), lower haloalkoxy group (for example, chloroethoxy group, bromopropoxy group and the like), lower cyanoalkoxy group (for example, cyanoethoxy group, cyanopropoxy group and the like), lower cycloalkyl group (for example, cyclopropyl group, cyclobutyl group, cyclopentyl group, and the like), group

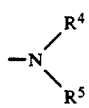

wherein $R^4$ and $R^5$ may be the same or different and represent hydrogen atom, lower alkyl group (for example, methyl group, ethyl group, propyl group and the like), lower alkenyl group (for example, vinyl group, allyl group, butenyl group and the like), lower aralkyl group (for example, benzyl group, phenylethyl group and the like), or aryl group which may or may not have substituent groups (for example, phenyl group, naphtyl group, 2-fluorophenyl group, 2,4-difluorophenyl group and the like), and $R^4$ and $R^5$ may or may not form a ring of 5 to 6 members along with a carbon atom adjacently bonded thereto, phenyl group which may or may not have a substituent group (for example, phenyl group which may or may not be substituted singly or plurally, with substituent groups such as halogen atom, lower alkoxy group, lower acyloxy group, hydroxy group, amino group, lower alkyl group, nitro group and the like). Specific examples of the group

include amino group, methylamino group, dimethylamino group, ethylamino group, benzylamino group, N-benzyl-N-methylamino group, N-benzyl-N-ethylamino group, allylamino group, pyrrolidinyl group and piperidinyl group. Specific examples of phenyl group which may or may not have a substituent group include phenyl group, 2-fluorophenyl group, 4-fluorophenyl group, 2,4-difluorophenyl group, 2-hydroxyphenyl group, 4-hydroxyphenyl group, 2-methoxyphenyl group, 4-methoxyphenyl group, 2-fluoro-4-methoxyphenyl group, 2-fluoro-4-hydroxyphenyl group, 4-methylphenyl group, 4-acetyloxyphenyl group, 4-aminophenyl group and 4-nitrophenyl group.

Most preferable examples of the lower alkyl group which may or may not have a substituent group, of the lower cycloalkyl group which may or may not have a substituent group, of the lower alkenyl group which may or may not have a substituent group, or of the lower alkynyl group which may or may not have a substituent group, all represented by $R^1$, are as follows:

Methyl group, ethyl group, n-propyl group, isopropyl group, butyl group, isobutyl group, fluoromethyl group, trifluoromethyl group, chloromethyl group, dichloroethyl group, cyanoethyl group, cyanopropyl group, cyanobutyl group, methoxymethyl group, methoxyethyl group, ethoxyethyl group, propoxyethyl group, isopropoxyethyl group, butoxyethyl group, methoxypropyl group, chloroethoxymethyl group, bromopropoxyethyl group, cyanoethoxymethyl group, cyanoethoxyethyl group, cyanoethoxypropyl group, cyanopropoxymethyl group, cyclopropylmethyl group, cyclobutylethyl group, cyclopentylmethyl group, aminomethyl group, aminoethyl group, methylaminomethyl group, ethylaminomethyl group, dimethylaminoethyl group, dimethylamino-n-propyl group, benzylaminomethyl group, N-benzyl-N-methylaminoethyl group, N-benzyl-N-ethylaminoethyl group, N-benzyl-N-methylamino-n-propyl group, N-benzyl-N-ethylamino-n-propyl group, piperidinyl group, cyclopropyl group, cyclobutyl group, cyclopentyl group, cyclohexyl group, vinyl group, allyl group, butenyl group, propargyl group, butynyl group, benzyl group, phenylethyl group, pheynlpropyl group, 4-fluorophenylmethyl group, 4-fluorophenylethyl group, 4-methylphenylmethyl group.

The lower alkyl group which may or may not have a substituent group, represented by $R^2$ and $R^3$, includes any one described above as $R^1$, and may preferably be methyl group, ethyl group, propyl group, chloromethyl group, dichloromethyl group and the like.

As the aryl group represented by X, which may or may not have a substituent group, there may be illustrated for example by phenyl group, naphtyl group and the like. As the unsaturated heterocyclic group represented by X, which may or may not have a substituent group, there may be illustrated for example by phenyl group, furyl group, pyryl group, pyrazolyl group, imidazoryl group, oxazoryl group, isoxazoryl group, thiazoryl group, pyridyl group, pyridazynyl group, pyrimizyl group, pyrazinyl group, benzofurazanyl group, methylenedioxyphenyl group and the like: the term unsaturated heterocyclic group means monocyclic and bicyclic heterocyclic group containing, as hetero atom, oxygen atom, sulfur atom and/or nitrogen atom. These groups may or may not be substituted with one to three groups selected from the group consisting of halogen atom, nitro group, lower haloalkyl group (for example, fluoromethyl group, dichloroethyl group, trifluoromethyl group and the like), lower haloalkoxy group (for example, chloroethoxy group, bromopropoxy group, difluoromethoxy group, trifluoromethoxy group and the like), lower haloalkoxyalkyl group (for example, chloroethoxymethyl group, bromopropoxyethyl group and the like), lower alkylsulfonyl group (for example, methylsulfonyl group, ethylsulfonyl group and the like), lower alkylsulfinyl group (for example, methylsulfinyl group, ethylsulfinyl group and the like), lower alkyl group (for example, methyl group, ethyl group and the like), lower alkoxy group (for example, methoxy group, ethoxy group, propoxy group and the like), lower cycloalkyl group (for example, cyclopropyl group, cyclobutyl group and the like), cyano group, lower alkoxycalbonyl group (for example, methoxycarbonyl group, ethoxycarbonyl group and the like) and lower alkylthio group (for example, methylthio group, ethylthio group and the like).

Specifically preferable examples of the aryl group which may or may not have a substituent group, or of the unsaturated heterocyclic group which may or may not have a substituent group, represented by X, are as follows:

3-Nitrophenyl group, 2-nitrophenyl group, 3-chlorophenyl group, 2-chlorophenyl group, 2,3-dichlorophenyl group, 3,4-dichlorophenyl group, 2,3,5-trichlorophenyl group, 2,3,6-trichlorophenyl group, 3-fluorophenyl group, 3,5-difluorophenyl group, 3-bromophenyl group, 2-nitro-5-fluorophenyl group, 2-nitro-6-fluorophenyl group, 3-nitro-5-fluorophenyl group, 3-nitro-6-fluorophenyl group, 3-trifluoromethylphenyl group, 2-trifluoromethylphenyl group, 2-chloro-3-trifluoromethylphenyl group, 2-trifluoromethyl-3-chlorophenyl group, 3-difluoromethoxyphenyl group, 2-difluoromethoxyphenyl group, 3-methylphenyl group, 2-methylphenyl group, 3-t-butylphenyl group, 3-methoxyphenyl group, 2-methoxyphenyl group, 3-trifluoromethoxyphenyl group, 2-trifluoromethoxyphenyl group, 3-cyanophenyl group, 2-cyanophenyl group, 3-methoxycarbonylphenyl group, 3-methylthiophenyl group, 2-methylthiophenyl group, 2-thienyl group, 3-thienyl group, 2-furyl group, 3-furyl group, 1-naphtyl group, 2-naphthyl group, 4-benzofurazanyl group, 2,3-methylenedioxyphenyl group.

The substituent group, which may or may not be bound to 3,4-dihydro-2H-benzo[b]pyran-4-yl group represented by Y and $R^1$, includes lower alkyl group (for example, methyl group, ethyl group and the like), lower alkoxy group (for example, methoxy group, ethoxy group and the like), halogen atom (for example, fluorine atom, chlorine atom, bromine atom and the like), lower haloalkyl group (for example, chloromethyl group, fluoromethyl group, difluoromethyl group, trifluoromethyl group and the like), lower haloalkoxy group (for example, difluoromethoxy group, trifluoromethoxy group and the like). cyano group, nitro group and the like, and 3,4-dihydro-2H-benzo[b]pyran- 4-yl group may or may not have a plurality of these substituent groups.

Further, specifically preferable examples of 3,4-dihydro-2H-benzo[b]pyran-4-yi group, which may or may not have a substituent group, represented by Y and $R^1$, are as follows:

3,4-Dihydro-2H-benzo[b]pyran-4-yl group,
3,4-dihydro-5-methyl-2H-benzo[b]pyran-4-yl group,
3,4-dihydro-6-methyl-2H-benzo[b]pyran-4-yl group,
3,4-dihydro-7-methyl-2H-benzo[b]pyran-4-yl group,
3,4-dihydro-8-methyl-2H-benzo[b]pyran-4-yl group,
3,4-dihydro-5-methoxy-2H-benzo[b]pyran-4-yl group,
3,4-dihydro-6-methoxy-2H-benzo[b]pyran-4-yl group,
3,4-dihydro-7-methoxy-2H-benzo[b]pyran-4-yl group,
3,4-dihydro-8-methoxy-2H-benzo[b]pyran-4-yl group,
3,4-dihydro-5-fluoro-2H-benzo[b]pyran-4-yl group,
3,4-dihydro-6-fluoro-2H-benzo[b]pyran-4-yl group,
3,4-dihydro-7-fluoro-2H-benzo[b]pyran-4-yl group,
3,4-dihydro-8-fluoro-2H-benzo[b]pyran-4-yl group,
3,4-dihydro-5-chloro-2H-benzo[b]pyran-4-yl group,
3,4-dihydro-6-chloro-2H-benzo[b]pyran-4-yl group,
3,4-dihydro-7-chloro-2H-benzo[b]pyran-4-yl group,
3,4-dihydro-8-chloro-2H-benzo[b]pyran-4-yl group,
3,4-dihydro-5-bromo-2H-benzo[b]pyran-4-yl group,
3,4-dihydro-6-bromo-2H-benzo[b]pyran-4-yl group,
3,4-dihydro-7-bromo-2H-benzo[b]pyran-4-yl group,
3,4-dihydro-8-bromo-2H-benzo[b]pyran-4-yl group,
3,4-dihydro-5-cyano-2H-benzo[b]pyran-4-yl group,
3,4-dihydro-6-cyano-2H-benzo[b]pyran-4-yl group,
3,4-dihydro-7-cyano-2H-benzo[b]pyran-4-yl group,
3,4-dihydro-8-cyano-2H-benzo[b]pyran-4-yl group,
3,4-dihydro-S-nitro-2H-benzo[b]pyran-4-yl group,
3,4-dihydro-6-nitro-2H-benzo[b]pyran-4-yl group,
3,4-dihydro-7-nitro-2H-benzo[b]pyran-4-yl group,
3,4-dihydro-8-nitro-2H-benzo[b]pyran-4-yl group,
3,4-dihydro-5-trifluoromethyl-2H-benzo[b]pyran-4-yl group,
3,4-dihydro-6-trifluoromethyl-2H-benzo[b]pyran-4-yl group,
3,4-dihydro-7-trifluoromethyl-2H-benzo[b]pyran-4-yl group,
3,4-dihydro-8-trifluoromethyl-2H-benzo[b]pyran-4-yl group,
3,4-dihydro-5-trifluoromethoxy-2H-benzo[b]pyran-4-yl group,
3,4-dihydro-6-trifluoromethoxy-2H-benzo[b]pyran-4-yl group,
3,4-dihydro-7-trifluoromethoxy-2H-benzo[b]pyran-4-yl group,
3,4-dihydro-8-trifluoromethoxy-2H-benzo[b]pyran-4-yl group,
3,4-dihydro-2,2-dimethyl-2H-benzo[b]pyran-4-yl group,
3,4-dihydro-2,2-dimethyl-5-methyl-2H-benzo[b]pyran-4-yl group,
3,4-dihydro-2,2-dimethyl-6-methyl-2H-benzo[b]pyran-4-yl group,
3,4-dihydro-2,2-dimethyl-7-methyl-2H-benzo[b]pyran-4-yl group,
3,4-dihydro-2,2-dimethyl-8-methyl-2H-benzo[b]pyran-4-yl group,
3,4-dihydro-2,2-dimethyl-5-methoxy-2H-benzo[b]pyran-4-yl group,
3,4-dihydro-2,2-dimethyl-6-methoxy-2H-benzo[b]pyran-4-yl group,
3,4-dihydro-2,2-dimethyl-7-methoxy-2H-benzo[b]pyran-4-yl group,
3,4-dihydro-2,2-dimethyl-8-methoxy-2H-benzo[b]pyran-4-yl group,
3,4-dihydro-2,2-dimethyl-5-fluoro-2H-benzo[]pyran-4-yl group,
3,4-dihydro-2,2-dimethyl-6-fluoro-2H-benzo[b]pyran-4-yl group,
3,4-dihydro-2,2-dimethyl-7-fluoro-2H-benzo[b]pyran-4-yl group,
3,4-dihydro-2,2-dimethyl-8-fluoro-2H-benzo[b]pyran-4-yl group,
3,4-dihydro-2,2-dimethyl-5-chloro-2H-benzo[b]pyran-4-yl group,
3,4-dihydro-2,2-dimethyl-6-chloro-2H-benzo[b]pyran-4-yl group,
3,4-dihydro-2,2-dimethyl-7-chloro-2H-benzo[b]pyran-4-yl group,
3,4-dihydro-2,2-dimethyl-8-chloro-2H-benzo[b]pyran-4-yl group,
3,4-dihydro-2,2-dimethyl-5-bromo-2H-benzo[b]pyran-4-yl group,
3,4-dihydro-2,2-dimethyl-6-bromo-2H-benzo[b]pyran-4-yl group,
3,4-dihydro-2,2-dimethyl-7-bromo-2H-benzo[b]pyran-4-yl group,
3,4-dihydro-2,2-dimethyl-8-bromo-2H-benzo[b]pyran-4-yl group,
3,4-dihydro-2,2-dimethyl-5-cyano-2H-benzo[b]pyran-4-yl group,
3,4-dihydro-2,2-dimethyl-6-cyano-2H-benzo[b]pyran-4-yl group,
3,4-dihydro-2,2-dimethyl-7-cyano-2H-benzo[b]pyran-4-yl group,
3,4-dihydro-2,2-dimethyl-8-cyano-2H-benzo[b]pyran-4-yl group,
3,4-dihydro-2,2-dimethyl-5-nitro-2H-benzo[b]pyran-4-yl group,
3,4-dihydro-2,2-dimethyl-6-nitro-2H-benzo[b]pyran-4-yl group,
3,4-dihydro-2,2-dimethyl-7-nitro-2H-benzo[b]pyran-4-yl group,
3,4-dihydro-2,2-dimethyl-8-nitro-2H-benzo[b]pyran-4-yl group.
3,4-dihydro-2,2-dimethyl-5-trifluoromethyl-2H-benzo[b]pyran-4-yl group, 3,4-dihydro-2,2-dimethyl-6-trifluoromethyl-2H-benzo[b]pyran-4-yl group, 3,4-dihydro-2,2-dimethyl-7-trifluoromethyl-2H-benzo[b]pyran-4-yl group, 3,4-dihydro-2,2-dimethyl-8-trifluoromethyl-2H-benzo[b]pyran-4-yl group, 3,4-dihydro-2,2-dimethyl-5-trifluoromethoxy-benzo[b]pyran-4-yl group, 3,4-dihydro-2,2-dimethyl-6-trifluoromethoxy-benzo[b]pyran-4-yl group, 3,4-dihydro-2,2-dimethyl-7-trifluoromethoxy-benzo[b]pyran-4-yl group,
3,4-dihydro-2,2-dimethyl-8-trifluoromethoxy-benzo[b]pyran-4-yl group, 3,4-dihydro-2,2-diethyl-2H-benzo[b]pyran-4-yl group,
3,4-dihydro-2,2-diethyl-5-fluoro-2H-benzo[b]pyran-4-yl group,
3,4-dihydro-2,2-diethyl-6-fluoro-2H-benzo[b]pyran-4-yl group,
3,4-dihydro-2,2-diethyl-7-fluoro-2H-benzo[b]pyran-4-yl group,
3,4-dihydro-2,2-diethyl-8-fluoro-2H-benzo[b]pyran-4-yl group,
3,4-dihydro-2,2-diethyl-5-cyano-2H-benzo[b]pyran-4-yl group,
3,4-dihydro-2,2-diethyl-6-cyano-2H-benzo[b]pyran-4-yl group, 3,4-dihydro-2,2-diethyl-7-cyano-2H-benzo[b]pyran-4-yl group,
3,4-dihydro-2,2-diethyl-8-cyano-2H-benzo[b]pyran-4-yl group,
3,4-dihydro-2,2-diethyl-5-nitro-2H-benzo[b]pyran-4-yl group,
3,4-dihydro-2,2-diethyl-6-nitro-2H-benzo[b]pyran-4-yl group,
3,4-dihydro-2,2-diethyl-7-nitro-2H-benzo[b]pyran-4-yl group,
3,4-dihydro-2,2-diethyl-8-nitro-2H-benzo[b]pyran-4-yl group.

Of the compounds represented by formula (I), of the present invention, those having basic groups can form salts with pharmaceutically acceptable acids. Such acids include mineral acids such as hydrochloric acid, hydrobromic acid, hydroiodic acid, sulfuric acid, nitric acid, phosphoric acid; and organic acids such as formic acid, acetic acid, oxalic acid, citric acid, succinic acid, fumaric acid, maleic acid, malic acid, tartaric acid, methanesulfonic acid, ethanesulfonic acid and the like.

The compounds (I) of the present invention have an asymmetric carbon, and all such optically active substances and the mixtures thereof are included within the scope of the present invention. The optically active compounds can be produced by using optically active starting materials. They can also be obtained by means of chromatography using an optically active carrier, by which racemic compounds are separated. Among the compounds represented by formula (I), those having basic properties may be obtained by the following steps: racemic compounds are reacted with an optically active acid (for example, tartaric acid, diacetyltartaric acid, tartranyl acid, dibenzoyltartaric acid, and ditoluoil acid) to form salts of diastereoisomer, followed by separation such as crystallization, evaporation, chromatography and the like, and optically active compounds are obtained from the separated salts.

The compound (I) of the present invention can be produced by either one of the following methods. However, the selection as to which method is used among them, depends on the kinds of the substituent groups.

Method 1

The compounds represented by formulae (II)–(IV)

  X—CHO (II)

  R³COCH₂COOY (III)

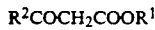  R²COCH₂COOR¹ (IV)

wherein R¹, R², R³, X and Y have the same meaning as described above, are reacted with ammonia to produce the compound (I) of the present invention.

This reaction can be carried out according to, for example, Hantzschpyridine synthetic method (Annalen der Chemie, 215, 1, 72(1882)).

Method 2

The compounds represented by formulae (II), (IV) and (V)

  X—CHO (III)

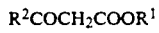  R²COCH₂COOR¹ (IV)

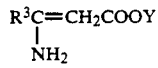
R³C=CH₂COOY (V)
|
NH₂ wherein R¹, R², R³, X and Y have the same meaning as described above, are reacted together to produce the compound (I) of the present invention.

This reaction can be carried out by mixing, for example, (II), (IV) and (V) and heating at a temperature range from room temperature to the refluxing temperature of a solvent to be used, more preferably from 60° C. to the refluxing temperature of the solvent to be used for 2 to 24 hours, in the presence of an appropriate solvent (for example methanol, ethanol, propanol, isopropanol, dioxane, benzene, toluene, acetonitrile, dimethylformamide, and dimethylsulfoxide).

Method 3

The compounds represented by the general formulae (II), (III) and (VI)

  X—CHO (II)

  R³COCH₂COOY (III)

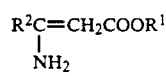
R²C=CH₂COOR¹ (VI)
|
NH₂ wherein R¹, R², R³, X and Y have the same meaning as described above, are reacted together to produce the compound (I) of the invention.

This reaction can be carried out under the same conditions as in Method 2 described above.

The compounds (IV) and (VI) can be obtained by reacting the compound (II) or (IV) with an ammonia or inorganic ammonium salt. The reaction is carried out by heating, for example, (IV) or (VI) with an ammonia or inorganic ammonium salt (for example ammonium chloride, ammonium sulfate, ammonium acetate and the like) at a temperature range from room temperature to the refluxing temperature of the solvent to be used, more preferably from 60° C. to the refluxing temperature of the solvent to be used for 2 to 24 hours in the presence of an appropriate solvent (for example, methanol, ethanol, propanol, isopropanol, dioxane, benzene, toluene, acetonitrile, dimethylformamide, and dimethylsulfoxide).

By treating the reaction mixture according to the ordinary method after termination of the reaction, the objective compound (I) can be obtained.

Depending on needs, further purification can be done by the ordinary method such as recrystallization, column chromatography and the like.

Action

Pharmaceutical actions of representative compounds of the present invention (I) are shown hereinbelow.

(1) Antihypertensive Actions

Test compounds were orally administered to spontaneous hypertensive rats (abbreviated as "SHR" hereinafter) to examine antihypertensive actions thereof.

That is, according to the method of Weeks and Jones (Weeks J. R. and Jones J. A., Proc. Soc. Exptl. Bil. Med., Vol.104, pp. 646–648(1960)), a catheter was retained to the aorta abdominalis of a SHR of 25 to 40 weeks old. Two to three days after the operation, the catheter was drawn out from the dorsum cervical part of the rat, and was connected to a blood-pressure measuring device (Polygraph RM-6000 manufactured by Nippon Koden K.K.). Blood pressure and heart rate were measured under the condition without anesthesia and restraint. The test compounds were suspended in 0.5% carboxymethylcellulose for oral administration. To the basal blood pressure obtained by measuring blood pressure over four hours, the lowest blood pressure decreased by the test compounds was used to determine the rate of blood-pressure decrease.

Rate of blood-pressure decrease
$(\%) = (A - B)/A \times 100$

A: Basal blood pressure
B: Lowest blood pressure

The results are shown in Table 1. The compound numbers correspond to those indicated in Examples.

TABLE 1

| Compound No. | Rate of blood pressure (%)* |
|---|---|
| 3 | 35.1 |
| 21 | 37.3 |
| 27 | 36.9 |
| Nifedipine | 24.3 |

*Rate of blood pressure decreases (%) when each sample of 10 mg/kg was orally administered.

(2) Calcium Antagonism

A guinea pig having a body weight ranging from 350 g to 400 g was exsanguinated to death and laparotomized, to extract ileum. According to the method of Rosenberger et al.(Rosenberger et al., Can. J. Physiol. Pharmacol. 57, 333-347(1979)), a sample of longitudinal muscle was prepared from the ileum. Then, a mixed gas consisting of 95% oxygen and 5% carbon dioxide was aerated, while the atmosphere was maintained at 37° C. The sample of the longitudinal muscle of the extracted ileum was placed in a magnus tube containing 20 ml of Tyrode solution, and suspended at 0.5 g of tension. As a comparison, 80 mM KCl was administered to contract the longitudinal muscle. Subsequently, 60 min after the addition of each of the test compounds ($10^{-8}$M), the contraction with KCl was again induced. The level of the contraction obtained by the administration of 80 mM KCl was assigned to 100%, and the inhibition rate thereto was determined. The results are shown in Table 2.

TABLE 2

| Compound No. | Inhibition rate (%) |
|---|---|
| 27 | 42 |
| 21 | 69 |
| 3 | 81 |
| Nifedipine | 98 |

(3) Acute Toxicity Test

Male ddY mice (5-7 weeks old) were divided into groups each consisting of 4 mice. The test compounds were dissolved in physiological saline containing 50% polyethylene glycol 400, which was then administered intravenously to the mice, and they were put under observation over two weeks. The analysis was done following the Van der Worden method. The results are shown in Table 3.

TABLE 3

| Compound No. | $LD_{50}$ (mg/kg) |
|---|---|
| 21 | 29.7 |
| Nifedipine | 5.3 |

As described above, the compound of the present invention had excellent antihypertensive action and calcium antagonism, with extremely low toxicity.

The compounds (I) of the present invention can be formulated with pharmaceutically acceptable carriers for parenteral administration through injection and rectum, and oral administration in the form of solid or liquid.

The form of the compositions of the present invention for injections includes pharmaceutically acceptable sterile water or non-aqueous solutions, suspensions or emulsions.

The solid preparation for oral administration includes capsules, tablets, pills, powders and granules. For the preparation of solid formulation, the compounds of the present invention are generally mixed with at least one of inert diluents, for example, sucrose, lactose or carbohydrate. The formulation can contain additive substances such as a lubricant (for example, magnesium stearate) other than inert diluents in the general formulation. In the case of capsules, tablets and pills, buffering agents can be contained. In the case of tablets and pills, enteric coating can be done as well. These solid formulations for oral administration can be prepared into the form to be dissolved hypoglossally.

Liquid formulations for oral administration include inert diluents containing water, generally used in the skilled person in the art, for example, pharmaceutically acceptable emulsion solutions, suspensions, syrups and elixirs. In addition to such inert diluents, there can be blended auxiliary agents for example emollients, emulsifying agents, suspensions and sweeteners, seasoning agents and spices.

The formulation for transrectum administration may be suppositories which may or may not contain vehicles for example cacao oils or suppository waxes besides the compound of the present invention.

Although the dose of the compound of the present invention depends on the properties, dosage regimen, desired duration of treatment and other factors, the dose is generally about 0.001 to 100 mg/kg per day, specifically preferably about 0.01 to 10 mg/kg per day. Furthermore, the dose per day may be divided in 2 to 4 for administration, depending on needs. The compounds of the present invention and salts thereof have excellent antihypertensive action and calcium antagonism, and are useful as therapeutic agents of cardiovascular diseases for humans and animals, such as prophylactic agents and treating agents of thrombosis, coronal circulation ameliorating agents, cerebrovascular dilating agents, diuretics and antihypertensive agents.

EXAMPLES

The present invention will now be explained in detail with reference to Examples and Reference Examples, but the present invention is not limited to these Examples.

When two types of diastereomers are used in the following examples, the isomer which is eluted earlier by silica column chromatography is tentatively designated as diastereomer A and the isomer eluted later is tentatively designated as diastereomer B.

REFERENCE EXAMPLES

Synthesis of 3,4-dihydro-2,2-dimethyl-2H-benzo[b]pyran-4-yl acetoacetate:

(1) Twenty five grams (25 g) of 2-hydroxyacetophenon, 10.7 g of acetone, and 5.5 g of pyrrolidine were added to 50 ml of toluene, and heated and refluxed. Twenty hours later, the temperature was returned to ambient temperature and the solvent was distilled off under reduced pressure, to which was added 100 ml of 1N hydrogen chloride. The extraction was carried out with 50 ml×3 of chloroform, followed by washing in water, drying over anhydrous magnesium sulfate, filtering off and condensation of the filtered solution. The residue was purified on a silica gel column the fraction containing the purified product were mixed together and the solvent therein was distilled off under reduced pressure to obtain 7 g of 3,4-dihydro-2,2-dimethyl-2H-benzo[b]pyran-4-one.

Melting point 88° to 90° C.

$^1$H-NMR (CDCl$_3$) δ ppm: 6.89–7.82 (m,4H), 2.71(s,2H), 1.44(s,6H).

(2) To 7 g of 3,4-dihydro-2,2-dimethyl-2H-benzo[b]-pyran-4-one obtained in (1), in a solvent of 50 ml ethanol, was added 1.5 g of sodium borohydride under agitation. After refluxing for 15 minutes, the solvent was distilled off. The residue was neutralized with 1N hydrogen chloride, and the extraction was carried out via chloroform, followed by washing of the organic layer in water, drying over anhydrous magnesium sulfate and filtering off, to condensate the filtered solution. To the residue were added 10 ml of benzene and 20 mg of sodium acetate. To the solution was added dropwise 3.3 g of diketene under agitation while keeping the temperature of the system at 80° to 90° C. After termination of the addition, the reaction was allowed to proceed at the same temperature for one and a half hour. After distilling off the solvent, the residue was purified by silica gel chromatography. The fraction containing the residue was concentrated to obtain 3.3 g of a colorless oily substance.

$^1$H-NMR (CDCl$_3$) δ ppm: 6.80–7.26(m,4H), 6.04–6.09(m,1H), 3.51(s,3H), 2,27(s,3H), 1.98–2.30(m,2H), 1.40(s,3H), 1.38(s,3H).

EXAMPLE 1

3-(3,4-dihydro-2H-benzo[b]pyran-4-yl) 5-methyl 1,4-dihydro-2,6-dimethyl-4-(2-chlorophenyl)pyridine-3,5-dicarboxylate (Compound 1)

2-Chlorobenzaldehyde (0.27 g), 0.21 g of aminocrotonic acid methylester and 0.45 g of 3,4-dihydro-2H-benzo[b]pyran-4-yl acetoacetate were added to 5 ml of ethanol, and refluxed. Six hours later, the temperature was returned to ambient temperature to distill off ethanol under reduced pressure. The residue was purified on a silica gel column, and the fractions containing the purified product were mixed together and the solvent therein was distilled off under reduced pressure to obtain 0.06 g of the title compound as a 1:1 mixture of A-diastereomer and B-diastereomer.

Properties: Colorless powder $^1$H-NMR (CDCl$_3$) δ ppm: 6.67–7.31(m,16H), 5.88(m,2H), 5.68(brs,2H), 5.31(s,1H), 5.32(s,1H), 4.24–4.29(m,2H), 4.07–4.11(m,1H), 3.89–3.93(m,1H), 3.56(s,3H), 3.55(s,3H), 2.32(s,3H), 2,31(s,3H), 2.27(s,6H), 1.90–2.23(m,4H).

EXAMPLE 2

The compounds 2 to 35, shown in Table 4, were synthesized as in Example 1. Each compound was obtained as a 1:1 mixture of diastereomer A and diastereomer B.

TABLE 4

Structure:

R¹OOC–C(=C(R²)–NH–C(R³)=C–COOY)–X–... (dihydropyridine with X and Y substituents)

$$\text{R}^1\text{OOC}\diagdown\text{C}=\text{C}(\text{R}^2)-\text{NH}-\text{C}(\text{R}^3)=\text{C}-\text{COOY, with X at 4-position}$$

| Compound No. | X | R² | R³ | Y | R¹ | Properties | NMR(CDCl₃)δ ppm |
|---|---|---|---|---|---|---|---|
| 2 | 3-Cl-phenyl | CH₃ | CH₃ | chroman-4-yl | CH₃ | Colorless Powder | 6.80–7.32(m, 16H), 5.91(m, 2H), 4.91(s, 2H), 4.15–4.29(m, 3H), 3.97–4.05(m, 1H), 3.61(s, 3H), 3.60(s, 3H), 2.34(s, 3H), 2.31(s, 3H), 2.29(s, 6H), 1.79–2.23(m, 4H) |
| 3 | 2,3-diCl-phenyl | CH₃ | CH₃ | " | CH₃ | Colorless Powder | 6.67–7.27(m, 14H), 5.88(m, 2H), 5.64(brs, 2H), 5.38(s, 1H), 5.37(s, 1H), 4.24–4.28(m, 2H), 4.09–4.13(m, 1H), 3.84–3.85(m, 1H), 3.56(s, 3H), 3.55(s, 3H), 2.33(s, 6H), 2.28(s, 6H), 1.93–2.19(m, 4H) |
| 4 | 2,4-diCl-phenyl | CH₃ | CH₃ | " | CH₃ | Colorless Powder | 6.80–7.34(m, 14H), 5.89–5.94(m, 2H), 5.66(brs, 2H), 4.89(s, 2H), 4.02–4.30(m, 4H), 3.614(s, 3H), 3.608(s, 3H), 2.36(s, 3H), 2.35(s, 3H), 2.32(s, 3H), 2.31(s, 3H), 1.88–2.27(m, 4H) |
| 5 | 2,4,5-triCl-phenyl | CH₃ | CH₃ | " | CH₃ | Colorless Powder | 6.69–7.28(m, 12H), 5.90–5.91(m, 2H), 5.81(m, 2H), 5.37(s, 1H), 5.35(s, 1H), 4.14–4.26(m, 3H), 3.82–3.95(m, 2H), 3.57(s, 3H), 3.56(s, 3H), 2.33(s, 6H), 2.29(s, 6H), 1.85–2.22(m, 4H) |
| 6 | 2,3,5-triCl-phenyl | CH₃ | CH₃ | " | CH₃ | Colorless Powder | 6.50–7.30(m, 6H), 5.85–5.97(m, 3H), 3.96–4.31(m, 2H), 3.47(s, 3H), 2.23(s, 3H), 2.21(s, 3H), 1.85–2.17(m, 2H) |
| 7 | 2-NO₂-phenyl | CH₃ | CH₃ | chroman-4-yl | CH₃ | Yellow Powder | 6.48–7.68(m, 16H), 5.71–5.92(m, 6H), 3.85–4.36(m, 4H), 3.53(s, 3H), 3.49(s, 3H), 2.31(s, 3H), 2.26(s, 3H), 2.25(s, 6H), 1.93–2.18(m, 4H) |

TABLE 4-continued

Structure: R¹OOC-[ring with X substituent]-COOY, with R², R³ and N-H

| Compound No. | X | R² | R³ | Y | R¹ | Properties | NMR(CDCl₃)δ ppm |
|---|---|---|---|---|---|---|---|
| 8 | 3-NO₂-phenyl | CH₃ | CH₃ | " | CH₃ | Yellow Powder | 6.68–8.12(m, 16H), 5.91(m, 2H), 5.72(brs, 2H), 5.03(brs, 2H), 3.92–4.38(m, 4H), 3.61(s, 6H), 2.40(s, 3H), 2.38(s, 3H), 2.35(s, 6H), 1.76–2.28(m, 4H) |
| 9 | 2-CF₃-phenyl | CH₃ | CH₃ | " | CH₃ | Colorless Powder | 6.67–7.50(m, 16H), 5.91(brs, 2H), 5.66(brs, 2H), 5.52(brs, 2H), 4.01–4.21(m, 3H), 3.88–3.98(m, 1H), 3.57(s, 3H), 3.56(s, 3H), 2.26(s, 6H), 2.25(s, 6H), 1.93–2.19(m, 4H) |
| 10 | 3-CF₃-phenyl | CH₃ | CH₃ | " | CH₃ | Colorless Powder | 6.71–7.52(m, 16H), 5.92(brs, 2H), 5.71(brs, 2H), 4.99(s, 2H), 3.82–4.33(m, 4H), 3.60(s, 6H), 2.36(s, 3H), 2.35(s, 3H), 2.33(s, 3H), 2.31(s, 3H), 1.73–2.27(m, 4H) |
| 11 | 2-CN-phenyl | CH₃ | CH₃ | " | CH₃ | Colorless Powder | 6.82–7.56(m, 16H), 5.98(brs, 2H), 5.85(brs, 2H), 5.22(s, 2H), 4.07–4.12(m, 2H), 3.76–3.84(m, 2H), 3.58(s, 6H), 2.32(s, 6H), 2.30(s, 6H), 1.86–2.10(m, 4H) |
| 12 | 3-CN-phenyl | CH₃ | CH₃ | " | CH₃ | Colorless Powder | 6.77–7.52(m, 16H), 5.89(brs, 2H), 5.75(brs, 2H), 4.95(s, 2H), 4.14–4.33(m, 3H), 3.86–3.95(m, 1H), 3.61(s, 3H), 3.60(s, 3H), 2.37(s, 3H), 2.36(s, 3H), 2.34(s, 3H), 2.32(s, 3H), 1.80–2.27(m, 4H) |
| 13 | 3-Br-phenyl | CH₃ | CH₃ | chroman-4-yl | CH₃ | Colorless Powder | 6.83–7.33(m, 16H), 5.91(m, 2H), 5.63(brs, 2H), 4.91(s, 1H), 4.89(s, 1H), 4.18–4.29(m, 3H), 3.95–4.06(m, 1H), 3.61(s, 6H), 2.36(s, 6H), 2.35(s, 6H), 1.79–2.26(m, 4H) |

TABLE 4-continued

Structure header: R¹OOC with X, COOY, R³, R², and N-H (dihydropyridine core)

| Compound No. | X | R² | R³ | Y | R¹ | Properties | NMR(CDCl$_3$)δ ppm |
|---|---|---|---|---|---|---|---|
| 14 | 3,5-difluorophenyl | CH$_3$ | CH$_3$ | " | CH$_3$ | Colorless Powder | 6.63–7.30(m, 14H), 5.97–6.62(m, 2H), 5.72(brs, 2H), 4.96(s, 2H), 3.90–4.38 (m, 4H), 3.66(s, 3H), 3.65(s, 3H), 2.39(s, 6H), 2.35(s, 3H), 2.34(s, 3H), 1.84–2.30(m, 4H) |
| 15 | 3-methoxyphenyl | CH$_3$ | CH$_3$ | " | CH$_3$ | Colorless Powder | 6.61–7.30(m, 16H), 5.89–5.91(m, 2H), 5.70(brs, 2H), 4.94(s, 1H), 4.92(s, 1H), 3.94–4.28(m, 4H), 3.72(s, 3H), 3.63(s, 3H), 3.61(s, 6H), 2.35(s, 3H), 2.33(s, 3H), 2.30(s, 3H), 2.27(s, 3H), 1.84–2.23(m, 4H) |
| 16 | 2-methylphenyl | CH$_3$ | CH$_3$ | " | CH$_3$ | Colorless Powder | 6.74–7.40(m, 16H), 5.84–5.89(m, 2H), 5.61(brs, 2H), 5.09(s, 1H), 5.03(s, 1H), 3.99–4.27(m, 4H), 3.57(s, 3H), 3.56(s, 3H), 2.33(s, 3H), 2.31(s, 3H), 2.28(s, 3H), 2.27(s, 3H), 2.17(s, 3H), 2.08(s, 3H), 1.81–2.21(m, 4H) |
| 17 | 2,3-dichlorophenyl | CH$_3$ | CH$_3$ | " | C$_2$H$_5$ | Colorless Powder | 6.69–7.35(m, 14H), 5.86–5.94(m, 2H), 5.64(brs, 2H), 5.39(s, 2H), 3.82–4.29(m, 8H), 2.31(s, 6H), 2.27(s, 6H), 1.90–2.27(m, 4H), 1.11–1.29(m, 6H) |
| 18 | 3-nitrophenyl | CH$_3$ | CH$_3$ | " | C$_2$H$_5$ | Yellow Powder | 6.68–8.13(m, 16H), 5.89(brs, 2H), 5.81(brs, 2H), 5.05(s, 1H), 5.03(s, 1H), 3.92–4.79(m, 8H), 2.38(s, 3H), 2.37(s, 3H), 2.34(s, 6H), 1.88–2.26(m, 4H), 1.11–1.28(m, 6H) |
| 19 | 2-chlorophenyl | CH$_3$ | CH$_3$ | 2-(2,2-dimethylchroman-4-yl) | CH$_3$ | Colorless Powder | 6.47–7.35(m, 16H), 5.97–6.02(m, 2H), 5.76(brs, 2H), 5.40(s, 1H), 5.34(s, 1H), 3.58(s, 3H), 3.57(s, 3H), 2.34(s, 3H), 2.31(s, 3H), 2.29(s, 3H), 2.28(s, 3H), 1.75–2.20(m, 4H), 1.42(s, 3H), 1.31(s, 3H), 1.30(s, 3H), 1.27(s, 3H) |

TABLE 4-continued

Structure: R¹OOC-C=C(R²)-N(H)-C(R³)=C-COOY with X on the central carbon

| Compound No. | X | R² | R³ | Y | R¹ | Properties | NMR(CDCl₃)δ ppm |
|---|---|---|---|---|---|---|---|
| 20 | 3-chlorophenyl | CH₃ | CH₃ | " | CH₃ | Colorless Powder | 6.69–7.26(m, 16H), 6.03(m, 1H), 5.96(m, 1H), 5.72(brs, 2H), 5.00(s, 1H), 4.96(s, 1H), 3.62(s, 3H), 3.61(s, 3H), 2.39(s, 3H), 2.36(s, 3H), 2.33(s, 3H), 2.32(s, 3H), 1.58–2.28(m, 4H), 1.43(s, 3H), 1.35(s, 3H), 1.33(s, 3H), 1.31(s, 3H) |
| 21 | 2,3-dichlorophenyl | CH₃ | CH₃ | " | CH₃ | Colorless Powder | 6.41–7.26(m, 14H), 5.98–6.01(m, 2H), 5.65(brs, 2H), 5.45(s, 1H), 5.40(s, 1H), 3.57(s, 3H), 3.56(s, 3H), 2.35(s, 3H), 2.32(s, 3H), 2.30(s, 3H), 2.28(s, 3H), 1.74–2.22(m, 4H), 1.42(s, 3H), 1.31(s, 3H), 1.30(s, 3H), 1.27(s, 3H) |
| 22 | 2,4-dichlorophenyl | CH₃ | CH₃ | " | CH₃ | Colorless Powder | 6.65–7.30(m, 14H), 5.95–6.04(m, 2H), 5.81(brs, 2H), 4.97(s, 1H), 4.92(s, 1H), 3.63(s, 3H), 3.62(s, 3H), 2.40(s, 3H), 2.36(s, 3H), 2.34(s, 3H), 2.32(s, 3H), 1.82–2.28(m, 4H), 1.44(s, 3H), 1.35(s, 3H), 1.32(s, 6H) |
| 23 | 2,3,5-trichlorophenyl | CH₃ | CH₃ | " | CH₃ | Colorless Powder | 6.43–7.28(m, 14H), 5.97–6.09(m, 2H), 5.87(brs, 2H), 5.42(s, 1H), 5.38(s, 1H), 3.58(s, 6H), 2.38(s, 3H), 2.34(s, 3H), 2.31(s, 3H), 2.30(s, 3H), 1.78–2.20(m, 4H), 1.45(s, 3H), 1.32(s, 6H), 1.29(s, 3H) |
| 24 | 3-nitrophenyl | CH₃ | CH₃ | " | CH₃ | Yellow Powder | 6.54–8.19(m, 16H), 6.03(m, 1H), 5.97(m, 1H), 5.77(brs, 2H), 5.13(s, 1H), 5.06(s, 1H), 3.62(s, 3H), 3.61(s, 3H), 2.43(s, 3H), 2.39(s, 3H), 2.37(s, 3H), 2.35(s, 3H), 1.81–2.27(m, 4H), 1.45(s, 3H), 1.34(s, 3H), 1.31(s, 6H) |

TABLE 4-continued

Structure: R¹OOC-[dihydropyridine with X at 4-position, COOY, R², R³, NH]

| Compound No. | X | R² | R³ | Y | R¹ | Properties | NMR(CDCl₃)δ ppm |
|---|---|---|---|---|---|---|---|
| 25 | 3-CN-phenyl | CH₃ | CH₃ | -CH(Ar)-CH₂-C(CH₃)₂-O- (chroman-type with gem-dimethyl) | CH₃ | Colorless Powder | 6.60–7.52(m, 16H), 5.90–6.03(m, 4H), 5.03(s, 1H), 4.98(s, 1H), 3.63(s, 3H), 3.61(s, 3H), 2.42(s, 3H), 2.38(s, 3H), 2.35(s, 3H), 2.34(s, 3H), 1.76–2.28(m, 4H), 1.44(s, 3H), 1.35(s, 3H), 1.31(s, 6H) |
| 26 | 3-Br-phenyl | CH₃ | CH₃ | " | CH₃ | Colorless Powder | 6.69–7.35(m, 16H), 6.04(m, 1H), 5.96(m, 1H), 5.83(s, 1H), 5.81(s, 1H), 4.98(s, 1H), 4.96(s, 3H), 3.62(s, 3H), 3.61(s, 3H), 2.39(s, 3H), 2.36(s, 3H), 2.33(s, 3H), 2.31(s, 3H), 1.82–2.28(m, 4H), 1.43(s, 3H), 1.34(s, 6H), 1.31(s, 3H) |
| 27 | 2,3-diCl-phenyl | CH₃ | CH₃ | " | C₂H₅ | Colorless Powder | 6.46–7.31(m, 14H), 5.98–6.03(m, 2H), 5.71(brs, 2H), 5.46(s, 1H), 5.41(s, 1H), 4.00–4.08(m, 4H), 2.33(s, 3H), 2.30(s, 3H), 2.29(s, 3H), 2.28(s, 3H), 1.79–2.19(m, 4H), 1.42(s, 3H), 1.32(s, 3H), 1.30(s, 3H), 1.28(s, 3H), 1.11–1.18(m, 6H) |
| 28 | 1-naphthyl | CH₃ | CH₃ | chroman-4-yl | CH₃ | Colorless Powder | 6.41–8.30(m, 22H), 6.63–6.79(m, 6H), 4.02–4.31(m, 2H), 3.55–3.70(m, 2H), 3.38(s, 3H), 3.34(s, 3H), 2.42(s, 3H), 2.35(s, 3H), 2.32(s, 6H), 1.66–2.20(m, 4H) |
| 29 | 2-thienyl | CH₃ | CH₃ | " | CH₃ | Colorless Powder | 6.75–7.30(m, 14H), 5.94–5.97(m, 2H), 5.66(brs, 2H), 5.09(s, 2H), 4.14–4.29(m, 3H), 3.96–4.05(m, 1H), 3.66(s, 3H), 3.65(s, 3H), 2.35(s, 3H), 2.33(s, 3H), 2.31(s, 3H), 2.28(s, 3H), 1.81–2.27(m, 4H) |
| 30 | 2-furyl | CH₃ | CH₃ | " | CH₃ | Colorless Powder | 6.80–7.33(m, 10H), 5.76–6.21(m, 8H), 5.14(s, 2H), 4.17–4.30(m, 4H), 3.663(s, 3H), 3.659(s, 3H), 2.34(s, 3H), 2.32(s, 6H), 2.31(s, 3H), 1.95–2.27(m, 4H) |

TABLE 4-continued

![structure: R¹OOC-C=C(R²)-NH-C(R³)=C(COOY)-CH(X)- (dihydropyridine)]

| Compound No. | X | R² | R³ | Y | R¹ | Properties | NMR(CDCl₃) δ ppm |
|---|---|---|---|---|---|---|---|
| 31 | 2,3-dichlorophenyl | CH₃ | CH₃ | 2,2-dimethylchroman-4-yl | CH₃ | Colorless Powder | 6.41–7.26(m, 14H), 5.95–6.01(m, 2H), 5.71(brs, 2H), 5.44(s, 1H), 5.40(s, 1H), 3.57(s, 3H), 3.56(s, 3H), 2.36(s, 3H), 2.33(s, 3H), 2.31(s, 3H), 2.29(s, 3H), 1.89–2.18(m, 4H), 1.50–1.82(m, 8H), 0.82–0.95(m, 12H) |
| 32 | 3-nitrophenyl | CH₃ | CH₃ | " | CH₃ | Yellow Powder | 6.49–8.09(m, 16H), 6.11(brs, 2H), 5.94–6.03(m, 2H), 5.12(s, 1H), 5.05(s, 1H), 3.62(s, 6H), 2.43(s, 3H), 2.38(s, 3H), 2.36(s, 3H), 2.34(s, 3H), 1.93–2.28(m, 4H), 1.54–1.83(m, 8H), 0.80–0.94(m, 12H) |
| 33 | 3-chlorophenyl | CH₃ | CH₃ | " | CH₃ | Colorless Powder | 6.67–7.27(m, 16H), 5.91–6.05(m, 4H), 4.99(s, 1H), 4.95(s, 1H), 3.62(s, 6H), 2.38(s, 3H), 2.34(s, 3H), 2.32(s, 3H), 2.30(s, 3H), 1.90–2.30(m, 4H), 1.51–1.85(m, 8H), 0.83–0.94(m, 12H) |
| 34 | 2,3-dichlorophenyl | CH₃ | CH₃ | 2,2-dimethyl-7-methylchroman-4-yl | CH₃ | Colorless Powder | 6.22–7.28(m, 12H), 5.95–6.04(m, 2H), 5.90(brs, 2H), 5.48(s, 1H), 5.41(s, 1H), 3.58(s, 3H), 3.56(s, 3H), 2.36(s, 3H), 2.31(s, 3H), 2.29(s, 3H), 2.28(s, 3H), 2.23(s, 3H), 2.05(s, 3H), 1.72–2.16(m, 4H), 1.43(s, 3H), 1.30(s, 6H), 1.26(s, 3H) |
| 35 | 3-nitrophenyl | CH₃ | CH₃ | " | CH₃ | Yellow Powder | 6.37–8.09(m, 14H), 5.94–6.01(m, 2H), 5.78(brs, 2H), 5.14(s, 1H), 5.07(s, 1H), 3.63(s, 3H), 3.61(s, 3H), 2.45(s, 3H), 2.40(s, 3H), 2.38(s, 3H), 2.36(s, 3H), 2.25(s, 3H), 2.06(s, 3H), 1.79–2.32(m, 4H), 1.45(s, 3H), 1.34(s, 3H), 1.31(s, 3H), 1.30(s, 3H) |

EXAMPLE 3

3-(3,4-dihydro-2H-benzo[b]pyran-4-yl 5-isopropyl 1,4-dihydro-2,6-dimethyl-1-4-(3-nitrophenyl)pyridine-3,5-dicarboxylate (Compound 36)

3,4-dihydro-2H-benzo[b]pyran-4-yl acetoacetate (0.8 g) and 0.27 g of ammonium acetate were added to 5 ml of ethanol and refluxed. Thirty minutes later, 0.52 g of 3-nitrobenzaidehyde and 0.50 g of isopropyl acetoacetate were added to the mixture. Seven hours later, the temperature was returned to ambient temperature and the ethanol was distilled off under reduced pressure. The residue was purified on a silica column and the fractions containing the purified product were mixed together to distill off the solvent under reduced pressure, and consequently 0.6 g of the compound as a 1:1 mixture of diastereomer A and diastereomer B was obtained.

Properties: Colorless powder $^1$H-NMR (CDCl$_3$) δ ppm: 6.67–8.13(m,16H), 5.88–5.96(m,4H), 4.90–5.07(m,6H), 4.14–4.32(m,3H), 3.82–4.04(m,1H), 2.35(s,6H), 2.33(s,6H), 1,81–2,27(m,4H), 1.06–1,27(m,12H).

EXAMPLE 4

As in Example 3, the compounds 37 to 52 as shown in Table 5 were synthesized. Each compound was obtained as a 1:1 mixture of diastereomer A and diastereomer B.

TABLE 5

![Structure: dihydropyridine with R¹OOC, COOY, X, R², R³, N-H]

| Compound NO. | X | R² | R³ | Y | R¹ | Properties | NMR (CDCl₃) δ ppm |
|---|---|---|---|---|---|---|---|
| 37 | 3-NO₂-phenyl | CH₃ | CH₃ | chroman-4-yl | CH₂=CHCH₂— | Yellow Powder | 6.68–8.12(m, 16H), 6.03(brs, 2H), 5.79–5.90(m, 4H), 5.07–5.22 (m, 6H), 4.51–4.55(m, 4H), 4.12–4.29(m, 3H), 3.90–4.02(m, 1H), 2.37(s, 6H), 2.34(s, 6H), 1.82–2.27(m, 4H) |
| 38 | " | CH₃ | CH₃ | " | cyclopropylmethyl (CH₂–CH(CH₂CH₂)) | Yellow Powder | 6.65–8.18(m, 16H), 5.75–5.89(m, 4H), 5.16(s, 1H), 5.07(s, 1H), 3.79–4.30(m, 8H), 2.37(s, 6H), 2.34(s, 6H), 4.12–4.29(m, 4H), 1.04–1.07(m, 2H), 0.47–0.53(m, 4H), 0.17–0.22(m, 4H) |
| 39 | " | CH₃ | CH₃ | " | NCCH₂CH₂— | Yellow Powder | 6.81–8.05(m, 16H), 5.90–5.93(m, 4H), 5.04(s, 2H), 4.18–4.30(m, 7H), 3.94–4.04(m, 1H), 2.58–2.63(m, 4H), 2.37(s, 6H), 2.36(s, 6H), 1.86–2.20(m, 4H) |
| 40 | " | CH₃ | CH₃ | " | CH₃OCH₂CH₂— | Yellow Powder | 6.67–8.06(m, 16H), 5.88(brs, 2H), 5.78(brs, 2H), 5.06(s, 2H), 4.11–4.30(m, 7H), 3.90–3.98(m, 1H), 3.50(m, 4H), 3.33(s, 3H), 3.29(s, 3H), 2.40(s, 3H), 2.39(s, 3H), 2.34(s, 6H), 1.82–2.28(m, 4H) |
| 41 | " | CH₃ | CH₃ | " | CH₃N(CH₂Ph)CH₂— | Yellow Powder | 6.69–8.05(m, 26H), 6.19(brs, 2H), 5.90(brs, 2H), 5.06(s, 2H), 4.11–4.24(m, 7H), 3.90–3.98(m, 1H), 3.51–3.52(m, 4H), 2.61–2.66 (m, 4H), 2.38(s, 3H), 2.36(s, 3H), 2.32(s, 6H), 2.20(s, 3H), 2.17 (s, 3H), 1.85–2.26(m, 4H) |
| 42 | 3-NO₂-phenyl | CH₃ | CH₃ | chroman-4-yl | CH(CH₃)₂ | Yellow Powder | 6.65–8.04(m, 12H), 6.84–6.93(m, 2H), 6.69(brs, 1H), 4.98(brs, 1H), 5.37(s, 2H), 3.74–4.34(m, 2H), 2.35(s, 3H), 1.83–2.24(m, 2H) |
| 43 | 2,3-Cl₂-phenyl | CH₃ | CH₃ | " | CH₃CH(CH₃)— | Colorless Powder | 6.67–7.27(m, 14H), 5.87–5.92(m, 2H), 5.67(brs, 1H), 5.64(brs, 1H), 5.37(s, 2H), 4.87–4.97(m, 2H), 4.11–4.26(m, 3H), 3.84–3.94 (m, 1H), 2.29(s, 3H), 2.28(s, 3H), 2.27(s, 3H), 2.26(s, 3H), 1.91–2.23(m, 4H), 1.17–1.21(m, 6H), 0.98–1.01(m, 6H) |
| 44 | " | CH₃ | CH₃ | " | CH₂=CHCH₂— | Colorless Powder | 6.69–7.31(m, 14H), 5.71–5.91(m, 6H), 5.41(m, 2H), 5.10–5.12(m, |

TABLE 5-continued

Structure header: R¹OOC, COOY, X, R², R³, N-H pyridine core

| Compound NO. | X | R² | R³ | Y | R¹ | Properties | NMR (CDCl₃) δ ppm |
|---|---|---|---|---|---|---|---|
| 45 | (2,3-dichlorophenyl) | CH₃ | CH₃ | (4-methyl-2,2-dimethylchroman) | CH₂(CH-CH₂)CH₂ (cyclopropylmethyl) | Colorless Powder | 2H), 5.05–5.08(m, 2H), 5.41(s, 1H), 5.42(s, 3H), 2.28(s, 6H), 1.92–2.23(m, 4H) |
| 46 | " | CH₃ | CH₃ | " | NCCH₂CH₂— | Colorless Powder | 6.69–7.31(m, 14H), 6.02(brs, 2H), 5.86–5.92(m, 2H), 5.38(s, 1H), 5.36(s, 1H), 4.10–4.28(m, 7H), 3.80–3.92(m, 1H), 2.56–2.61(m, 4H), 2.30(s, 6H), 2.29(s, 6H), 1.92–2.23(m, 4H) |
| 47 | " | CH₃ | CH₃ | " | CH₃ NCH₂— / Ph—CH₂ | Colorless Powder | 6.69–7.31(m, 14H), 5.85–5.88(m, 2H), 5.68(brs, 2H), 5.38(s, 1H), 5.37(m, 1H), 4.10–4.23(m, 7H), 3.79–3.88(m, 1H), 3.44–3.45(m, 4H), 2.50–2.60(m, 4H), 2.32(s, 6H), 2.26(s, 6H), 2.15(s, 3H), 2.13(s, 3H), 1.88–2.26(m, 4H) |
| 48 | " | CH₃ | CH₃ | " | CH₃ CH— / CH₃ | Colorless Powder | 6.51–7.32(m, 14H), 5.99–6.04(m, 2H), 5.69(brs, 2H), 5.45(s, 1H), 5.39(s, 1H), 4.90–4.98(m, 2H), 2.32(s, 3H), 2.30(s, 3H), 2.29(s, 3H), 2.28(s, 3H), 1.96–2.18(m, 4H), 1.42(s, 3H), 1.32(s, 3H), 1.31(s, 3H), 1.28(s, 3H), 1.18–1.25(m, 6H), 0.99–1.02(m, 6H) |
| 49 | " | CH₃ | CH₃ | " | CH₂=CHCH₂— | Colorless Powder | 6.44–7.31(m, 14H), 6.00–6.03(m, 2H), 5.76–5.84(m, 4H), 5.48(s, 1H), 5.43(s, 1H), 5.07–5.12(m, 4H), 4.49–4.50(m, 4H), 2.34(s, 3H), 2.30(s, 3H), 2.29(s, 3H), 2.28(s, 3H), 1.74–2.20(m, 4H), 1.42(s, 3H), 1.32(s, 3H), 1.30(s, 3H), 1.28(s, 3H) |
| 50 | " | CH₃ | CH₃ | " | NCCH₂CH₂— | Colorless Powder | 6.44–7.33(m, 14H), 5.97–6.04(m, 2H), 5.78(brs, 2H), 5.44(s, 1H), 5.39(s, 1H), 4.16–4.24(m, 4H), 2.57–2.62(m, 4H), 2.35(s, 3H), 2.32(s, 3H), 2.31(s, 3H), 1.74–2.22(m, 4H), 1.42(s, 3H), 1.32(s, 3H), 1.30(s, 3H), 1.28(s, 3H) |
| 51 | " | CH₃ | CH₃ | " | CH₃ NCH₂CH₂— / Ph—CH₂ | Colorless Powder | 6.44–7.30(m, 24H), 5.97–6.02(m, 2H), 5.86(brs, 2H), 5.45(s, 1H), 5.40(s, 1H), 4.10–4.17(m, 4H), 3.44(s, 4H), 2.51–2.62(m, 4H), 2.33(s, 3H), 2.29(s, 3H), 2.27(s, 3H), 2.26(s, 3H), 2.15(s, 3H), 2.14(s, 3H), 1.78–2.26(m, 4H), 1.40(s, 3H), 1.31(s, 3H), 1.29(s, 3H), 1.28(s, 3H) |

TABLE 5-continued

| Compound NO. | X | R² | R³ | Y | R¹ | Properties | NMR (CDCl₃) δ ppm |
|---|---|---|---|---|---|---|---|
| 52 | 3-NO₂-phenyl | CH₃ | CH₃ | " | " | Yellow Powder | 6.54–8.09(m, 24H), 5.92–6.04(m, 4H), 5.14(s, 1H), 5.07(s, 1H), 4.12–4.17(m, 4H), 3.45(s, 2H), 2.56–2.62(m, 4H), 2.43(s, 3H), 2.39(s, 3H), 2.35(s, 3H), 2.33(s, 3H), 2.15(s, 6H), 1.79–2.28(m, 4H), 1.42(s, 3H), 1.34(s, 3H), 1.31(s, 3H), 1.30(s, 3H) |

EXAMPLE 5

3-(3,4-dihydro-2,2-dimethyl 2H-benzo[b]pyran-4-yl) 5-ethyl 1,4-dihydro-2,6-dimethyl-4-(2,3-dichlorophenyl)pyridine-3,5-dicarboxylate (Compound 53, 54)

A 1:1 mixture (0.1 g) of diastereomer A and diastereomer B of 3-(3,4-dihydro-2,2-dimethyl-2H-benzo[b]pyran-4-yl)5-ethyl 1,4-dihydro-2,6-dimethyl-4-(2,3-dichlorophenyl)pyridine-3,5-dicarboxylate (Compound 27) was purified several times on a silica column.

The fractions eluted earlier were collected and evaporated under reduced pressure to obtain 15 mg of the compound diastereomer A (Compound 53). The fractions eluted later were collected and evaporated under reduced pressure to obtain 15 mg of the compound diastereomer B (Compound 54).

Diastereomer A (Compound 53)

Properties: Colorless powder $^1$H-NMR (CDCl$_3$) δ ppm: 6.77–7.23(m,7H), 6.00(dd,1H,J=7Hz,8Hz), 5.64(brs,1H), 5.46(s,1H), 4.03(q,2H,J=7Hz), 2.34(s,3H), 2.31(s,3H), 2.01(dd,1H,J=7Hz,J=13.5Hz), 1.79(dd,1H,J=13.5Hz), 1.30(s,3H), 1.28(s,3H), 1.14(t,3H,J=7Hz)

Diastereomer B (Compound 54)

Properties: Colorless powder $^1$H-NMR (CDCl$_3$) δ ppm: 6.46–7.26(m,7H), 6.01(dd,1H,J=7Hz,8Hz), 5.68(brs,1H), 5.41(s,1H), 4.03(q,2H,J=7Hz), 2.34(s,3H), 2.28(s,3H), 2.14(dd,1H,J=7Hz,J=13.5Hz), 2.05(dd,1H,J=8Hz, J=13.5Hz), 1.42(s,3H), 1.32(s,3H), 1.13(t,3H,J=7Hz)

EXAMPLE 6

As in Example 5, from a 1:1 mixture of diastereomer A and diastereomer B of 3-(3,4-dihydro-2,2-dimethyl-2H-benzo[b]pyran-4-yl) 5-methtyl 1,4-dihydro-2,6-dimethyl-4-(2,3-dichorophenyl)pyridine-3,5-dicarboxylate (Compound 21), individual isomers were separated and purified.

Diastereomer A (Compound 55)

Properties: Colorless crystal

Melting point 107°–110° C.

$^1$H-NMR (CDCl$_3$) δ ppm: 6.78–7.26(m,7H), 6.01(dd,1H,J=7Hz,J=8Hz), 5.73(brs,1H), 5.45(s,1H), 3.57(s,3H), 2.31(s,3H), 2.30(s,3H), 1.97(dd,1H,J=7Hz,J=13.5Hz), 1.79(dd,1H,J=8Hz,J=13.5Hz), 1.30(s,3H), 1.27(s,3H).

Diastereomer B (Compound 56)

Properties: Colorless powder 6.40–7.27(m,7H), 6.01(dd,1H,J=7Hz,J=8Hz), 5.70(brs,1H), 5.40(s,1H), 3.56(s,3H), 2.36(s,3H), 2.30(s,3H), 2.15(dd,1H,J=7Hz,J=13.5Hz), 2.02(dd,1H,J=8Hz,J=13.5Hz), 1.43(s.3H), 1.32(s,3H).

EXAMPLE 7

As in Example 1, the Compounds 57 to 67 as shown in Table 6 were synthesized. Each compound was obtained as a 1:1 mixture of diastereomer A and diastereomer B.

TABLE 6

![Structure: R¹OOC-C=C(R²)-NH-C(R³)=C-COOY with X substituent]

| Compound No. | X | R² | R³ | Y | R¹ | Properties | NMR(CDCl₃) δ ppm |
|---|---|---|---|---|---|---|---|
| 57 | 3-NO₂-phenyl | CH₃ | CH₃ | 2-(2,2-dimethylchroman-4-yl) | CH₃ | Yellow Powder | 6.73–8.09(m, 14H), 5.85–6.06(m, 4H), 5.14(s, 1H), 5.05(s, 1H), 3.72(s, 3H), 3.62(s, 3H), 3.61(s, 3H), 3.55(s, 3H), 2.44(s, 3H), 2.39(s, 3H), 2.37(s, 3H), 2.35(s, 3H), 1.75–2.35(m, 4H), 1.44(s, 3H), 1.33(s, 3H), 1.30(s, 3H), 1.29(s, 3H) |
| 58 | 2,3-dichlorophenyl | CH₃ | CH₃ | 2-(2,2-dimethylchroman-4-yl) | CH₃ | Colorless Powder | 6.69–7.26(m, 14H), 5.99–6.03(m, 2H), 5.78(brs, 2H), 5.47(s, 1H), 5.39(s, 1H), 3.70(s, 3H), 3.58(s, 3H), 3.56(s, 3H), 3.54(s, 3H), 2.35(s, 3H), 2.32(s, 3H), 2.30(s, 3H), 2.29(s, 3H), 1.72–2.15(m, 4H), 1.43(s, 3H), 1.29(s, 6H), 1.26(s, 3H) |
| 59 | 3-NO₂-phenyl | CH₃ | CH₃ | 2-(2,2-dimethylchroman-4-yl) with CN | CH₃ | Yellow Powder | 6.77–8.06(m, 14H), 5.90–6.02(m, 2H), 5.86(brs, 2H), 5.11(s, 1H), 5.02(s, 1H), 3.64(s, 3H), 3.63(s, 3H), 2.46(s, 3H), 2.43(s, 3H), 2.39(s, 3H), 2.35(s, 3H), 1.81–2.30(m, 4H), 1.49(s, 3H), 1.38(s, 3H), 1.35(s, 3H), 1.33(s, 3H) |
| 60 | 2,3-dichlorophenyl | CH₃ | CH₃ | 2-(2,2-dimethylchroman-4-yl) with CN | CH₃ | Colorless Powder | 6.42–7.50(m, 14H), 5.94–6.09(m, 2H), 5.81(brs, 2H), 5.44(s, 1H), 5.35(s, 1H), 3.59(s, 3H), 3.57(s, 3H), 2.42(s, 3H), 2.37(s, 3H), 2.33(s, 3H), 2.31(s, 3H), 1.65–2.16(m, 4H), 1.50(s, 3H), 1.33(s, 3H), 1.31(s, 3H), 1.28(s, 3H) |
| 61 | 3-NO₂-phenyl | CH₃ | CH₃ | 2-(2,2-dimethylchroman-4-yl) with Cl | CH₃ | Yellow Powder | 6.46–8.08(m, 14H), 5.88–5.99(m, 2H), 5.83(brs, 2H), 5.13(s, 1H), 5.03(s, 1H), 3.64(s, 3H), 3.62(s, 3H), 2.45(s, 3H), 2.41(s, 3H), 2.38(s, 3H), 2.35(s, 3H), 1.74–2.32(m, 4H), 1.45(s, 3H), 1.33(s, 3H), 1.32(s, 3H), 1.30(s, 3H) |

TABLE 6-continued

![structure: R1OOC-/-COOY with X substituent, R2 and R3 on pyridine ring with NH]

| Compound No. | X | R² | R³ | Y | R¹ | Properties | NMR(CDCl₃) δ ppm |
|---|---|---|---|---|---|---|---|
| 62 | 2,3-dichlorophenyl | CH₃ | CH₃ | 4-(4-chlorophenyl)-4-methyl-2-(1,1-dimethyl)chroman-type group | CH₃ | Colorless Powder | 6.26–7.28(m, 1H), 5.91–6.01(m, 2H), 5.78(brs, 2H), 5.45(s, 1H), 5.36(s, 1H), 3.59(s, 3H), 3.57(s, 1H), 2.37(s, 3H), 2.34(s, 3H), 2.31(s, 3H), 2.30(s, 3H), 1.70–2.14(m, 4H), 1.45(s, 3H), 1.29(s, 6H), 1.25(s, 3H) |
| 63 | 3-cyanophenyl | CH₃ | CH₃ | 6-methylchroman derivative | CH₃ | Colorless Powder | 6.41–7.53(m, 14H), 5.93–6.00(m, 2H), 5.85(brs, 2H), 5.05(s, 1H), 4.99(s, 1H), 3.63(s, 3H), 3.61(s, 3H), 2.43(s, 3H), 2.39(s, 3H), 2.35(s, 3H), 2.34(s, 3H), 2.25(s, 3H), 2.12(s, 3H), 1.74–2.20(m, 4H), 1.44(s, 3H), 1.34(s, 3H), 1.29(s, 6H) |
| 64 | 3-cyanophenyl | CH₃ | CH₃ | 6-cyanochroman derivative | CH₃ | Colorless Powder | 6.76–7.54(m, 14H), 6.10(brs, 2H), 5.90–6.00(m, 2H), 5.02(s, 1H), 4.93(s, 1H), 3.64(s, 3H), 3.62(s, 3H), 2.44(s, 3H), 2.41(s, 3H), 2.361(s, 3H), 2.355(s, 3H), 1.72–2.28(m, 4H), 1.47(s, 3H), 1.35(s, 6H), 1.32(s, 3H) |
| 65 | 3-(OCF₃)phenyl | CH₃ | CH₃ | chroman (unsubstituted) | CH₃ | Light Yellow Powder | 6.75–7.36(m, 16H), 5.88–5.93(m, 2H), 5.83(brs, 2H), 4.96(s, 1H), 4.95(s, 1H), 3.89–4.31(m, 4H), 3.62(s, 3H), 3.60(s, 3H), 2.36(s, 3H), 2.34(s, 3H), 2.31(s, 3H), 2.29(s, 3H), 1.75–2.25(m, 4H) |
| 66 | 3-(OCF₃)phenyl | CH₃ | CH₃ | 2,2-dimethylchroman | CH₃ | Colorless Powder | 6.67–7.26(m, 16H), 5.96–6.03(m, 2H), 5.84(brs, 2H), 5.03(s, 1H), 5.00(s, 1H), 3.63(s, 3H), 3.62(s, 3H), 2.40(s, 3H), 2.38(s, 3H), 2.32(s, 6H), 1.75–2.06(m, 4H), 1.66(s, 3H), 1.42(s, 3H), 1.30(s, 6H) |
| 67 | 3-(OCF₃)phenyl | CH₃ | CH₃ | 6-methyl-2,2-dimethylchroman | CH₃ | Colorless Powder | 6.50–7.26(m, 14H), 5.93–6.03(m, 4H), 5.06(s, 1H), 5.02(s, 1H), 3.63(s, 3H), 3.62(s, 3H), 2.40(s, 3H), 2.38(s, 3H), 2.32(s, 3H), 2.31(s, 3H), 2.24(s, 3H), 2.11(s, 3H), 1.72–2.27(m, 4H), 1.42(s, 3H), 1.33(s, 3H), 1.29(s, 6H) |

EXAMPLE 8

TABLE 7

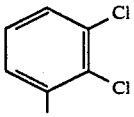

| Compound No. | X | R² | R³ | Y | R¹ | Properties | NMR (CDCl₃) δ ppm |
|---|---|---|---|---|---|---|---|
| 68 | 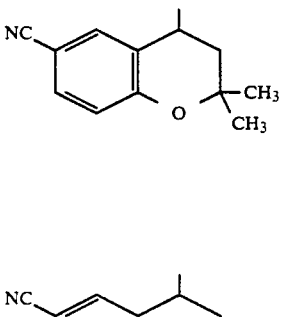 | CH₃ | CH₃ | 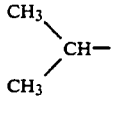 | $\underset{CH_3}{\overset{CH_3}{>}}CH-$ | Colorless Powder | 6.50–7.52(m, 14H), 5.89–6.07(m, 4H), 5.43(s, 1H), 5.33(s, 1H), 4.91–5.00 (m, 2H), 2.39(s, 3H), 2.34(s, 3H), 2.32(s, 3H), 2.29(s, 3H), 1.69–2.23 (m, 4H), 1.50(s, 3H), 1.35(s, 3H), 1.32(s, 3H), 1.30(s, 3H), 0.99–1.22 (m, 12H) |
| 69 | 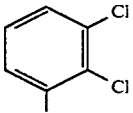 | CH₃ | CH₃ | 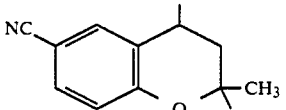 | 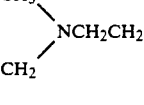 | Light Yellow Powder | 6.44–7.47(m, 22H), 5.93–6.06(m, 2H), 5.79(brs, 2H), 5.42(s, 1H), 5.35(s, 1H), 4.08–4.16(m, 4H), 3.44 (brs, 4H), 2.53–2.60(m, 4H), 2.41(s, 3H), 2.35(s, 3H), 2.31(s, 3H), 2.29(s, 3H), 2.15(s, 3H), 2.14(s, 3H), 1.67–2.26(m, 4H), 1.47 (s, 3H), 1.33(s, 3H), 1.31 (s, 3H), 1.28(s, 3H) |

As in Example 3, the Compounds 68 and 69 as shown in Table 7 were synthesized. Each compound was obtained as a 1:1 mixture of diastereomer A and diastereomer B.

EXAMPLE 9

The compounds 70 to 117 as shown in Table 8 were synthesized as in Example 1, and these racemic compounds were separated as in Example 3.

TABLE 8

| Compound No. | X | R₂ | R₃ | Y | R₁ | Steric type | Properties | NMR (CDCl₃) δ ppm |
|---|---|---|---|---|---|---|---|---|
| 70 | 3-CN-phenyl | CH₃ | CH₃ | 6-Cl-2,2-dimethylchroman-4-yl | CH₃ | Mix | Colorless Powder | 6.51–7.51(m, 14H), 5.87–5.96(m, 4H), 5.04(s, 1H), 4.94(s, 1H), 3.64(s, 3H), 3.62(s, 3H), 2.43(s, 3H), 2.39(s, 3H), 2.36(s, 3H), 2.33(s, 3H), 1.72–2.30(m, 4H), 1.44(s, 3H), 1.33(s, 3H), 1.30(s, 3H), 1.29(s, 3H) |
| 71 | " | CH₃ | CH₃ | " | CH₃ | A | Colorless Powder | 6.74–7.52(m, 7H), 5.92–5.97(m, 1H), 5.82(brs, 1H), 5.04(s, 1H), 3.64(s, 3H), 2.39(s, 3H), 2.36(s, 3H), 2.01–2.09(m, 1H), 1.69–1.78(m, 1H), 1.30(s, 3H), 1.29(s, 3H) |
| 72 | " | CH₃ | CH₃ | " | CH₃ | B | Colorless Crystal mp 210–212° C. | 6.51–7.51(m, 7H), 5.88–5.92(m, 1H), 5.76(brs, 1H), 3.62(s, 3H), 2.44(s, 3H), 2.34(s, 3H), 2.19–2.30(m, 1H), 1.89–1.98(m, 1H), 1.44(s, 3H), 1.33(s, 3H) |
| 73 | " | CH₃ | CH₃ | 6-CH₃-2,2-dimethylchroman-4-yl | CH₃ | A | Colorless Powder | 6.73–7.53(m, 7H), 5.98–6.02(m, 1H), 5.78(s, 1H), 5.05(s, 1H), 3.63(s, 3H), 2.39(s, 3H), 2.36(s, 3H), 2.25(s, 3H), 2.01–2.08(m, 1H), 1.74–1.82(m, 1H), 1.29(s, 6H) |
| 74 | " | CH₃ | CH₃ | " | CH₃ | B | Colorless Crystal mp 165–166° C. | 6.41–7.53(m, 7H), 5.93–6.06(m, 1H), 5.85(brs, 1H), 4.99(s, 1H), 3.61(s, 3H), 2.43(s, 3H), 2.34(s, 3H), 2.12(s, 3H), 1.92–2.21(m, 2H), 1.44(s, 3H), 1.34(s, 3H) |
| 75 | " | CH₃ | CH₃ | chroman-4-yl | iPr | Mix | Colorless Powder | 6.85–7.49(m, 16H), 5.72–5.87(m, 4H), 4.90–4.95(m, 4H), 3.73–4.32(m, 4H), 2.35(s, 3H), 2.34(s, 3H), 2.33(s, 3H), 2.32(s, 3H), 1.80–2.28(m, 4H), 1.07–1.22(m, 12H) |
| 76 | 3-CN-phenyl | CH₃ | CH₃ | chroman-4-yl | CH₃ | A | Colorless Crystal mp 135–136° C. | 6.85–7.49(m, 8H), 5.89(m, 1H), 5.68(brs, 1H), 4.14–4.20(m, 1H), 3.86–3.95(m, 1H), 3.60(s, 3H), 2.37(s, 3H), 2.32(s, 3H), 2.04–2.16(m, 1H), 1.80–1.88(m, 1H) |
| 77 | 3-NO₂-phenyl | CH₃ | CH₃ | " | CH₃ | A | Yellow Crystal mp 155–157° C. | 6.84–8.05(m, 8H), 5.91–5.92(m, 1H), 5.79(brs, 1H), 5.03(s, 1H), 4.16–4.22(m, 1H), 3.93–4.01(m, 1H), 3.61(s, 3H), 2.37(s, 3H), 2.34(s, 3H), 2.03–2.16(m, 1H), 1.82–1.88(m, 1H) |
| 78 | " | CH₃ | CH₃ | " | CH₃ | B | Yellow Powder | 6.70–8.06(m, 8H), 5.87–5.90(m, 1H), 5.78(brs, 1H), 5.01(s, 1H), 4.25–4.30(m, 2H), 3.61(s, 3H), 2.40(s, 3H), 2.34(s, 3H), 2.05–2.17(m, 2H) |

TABLE 8-continued

| Compound No. | X | R₂ | R₃ | Y | R₁ | Steric type | Properties | NMR (CDCl₃) δ ppm |
|---|---|---|---|---|---|---|---|---|
| 79 | " | CH₃ | CH₃ | 4-Cl-phenyl-CH(–)-CH₂-C(CH₃)₂-O- (chroman-type) | CH₃ | A | Yellow Crystal mp 128–131° C. | 6.74–8.08(m, 7H), 5.94–5.99(m, 1H), 5.78(brs, 1H), 5.13(s, 1H), 3.64(s, 3H), 2.41(s, 3H), 2.39(s, 3H), 2.01–2.08(m, 1H), 1.76–1.84(m, 1H), 1.32(s, 3H), 1.30(s, 3H) |
| 80 | 3-NO₂-phenyl | CH₃ | CH₃ | " | CH₃ | B | Yellow Powder | 6.46–8.04(m, 7H), 6.01(brs, 1H), 5.89–5.94(m, 1H), 5.03(m, 1H), 3.62(s, 3H), 2.45(s, 3H), 2.35(s, 3H), 2.18–2.28(m, 1H), 1.92–2.00(m, 1H), 1.45(s, 3H), 1.33(s, 3H) |
| 81 | 2,3-diCl-phenyl | CH₃ | CH₃ | 4-F-phenyl chroman-type | CH₃ | Mix | Yellow Powder | 6.12–8.09(m, 14H), 6.01(brs, 2H), 5.87–6.01(m, 2H), 5.13(s, 1H), 5.04(s, 1H), 3.64(s, 3H), 3.63(s, 3H), 2.45(s, 3H), 2.40(s, 3H), 2.36(s, 3H), 2.34(s, 3H), 1.77–2.27(m, 4H), 1.44(s, 3H), 1.32(s, 6H), 1.30(s, 3H) |
| 82 | " | CH₃ | CH₃ | 4-F-phenyl chroman-type | CH₃ | Mix | Yellow Powder | 6.72–8.09(m, 14H), 5.95–6.09(m, 2H), 5.84(brs, 2H), 5.14(s, 1H), 5.04(s, 1H), 4.14–4.28(m, 2H), 3.65(s, 3H), 3.63(s, 3H), 2.46(s, 3H), 2.40(s, 3H), 2.39(s, 3H), 2.35(s, 3H), 1.75–2.20(m, 4H), 1.41(d, 3H), 1.36(d, 3H) |
| 83 | " | CH₃ | CH₃ | 4-Cl-phenyl chroman-type | CH₃ | A | Colorless crystal mp 173–176° C. | 6.72–7.39(m, 6H), 5.91–5.98(m, 1H), 5.67(brs, 1H), 5.46(s, 1H), 3.59(s, 3H), 2.35(s, 3H), 2.32(s, 3H), 1.89–1.96(m, 1H), 1.68–1.89(m, 1H), 1.29(s, 3H), 1.25(s, 3H) |
| 84 | " | CH₃ | CH₃ | " | CH₃ | B | Colorless Powder | 6.26–7.30(m, 6H), 5.97–6.04(m, 1H), 5.71(brs, 1H), 5.37(s, 1H), 3.57(s, 3H), 2.39(s, 3H), 2.31(s, 3H), 2.04–2.17(m, 2H), 1.45(s, 3H), 1.30(s, 3H) |
| 85 | " | CH₃ | CH₃ | 4-F-phenyl chroman-type | CH₃ | Mix | Colorless Powder | 6.68–7.27(m, 12H), 5.92–6.01(m, 2H), 5.82(brs, 2H), 5.45(s, 1H), 5.37(s, 1H), 3.58(s, 3H), 3.58(s, 3H), 2.37(s, 3H), 2.33(s, 3H), 2.30(s, 3H), 2.29(s, 3H), 1.90–2.20(m, 4H), 1.44(s, 3H), 1.29(s, 6H), 1.25(s, 3H) |
| 86 | " | CH₃ | CH₃ | chroman | CH₃ | A | Colorless crystal mp 182–183° C. | 6.84–7.26(m, 7H), 5.87(m, 1H), 5.68(brs, 1H), 5.37(s, 1H), 4.09–4.13(m, 1H), 3.80–3.88(m, 1H), 3.55(s, 3H), 2.33(s, 3H), 2.28(s, 3H), 2.02–2.11(m, 1H), 1.89–1.95(m, 1H) |

TABLE 8-continued

| Compound No. | X | R₂ | R₃ | Y | R₁ | Steric type | Properties | NMR (CDCl₃) δ ppm |
|---|---|---|---|---|---|---|---|---|
| 87 | 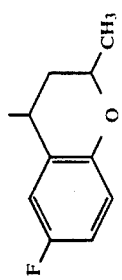 | CH₃ | CH₃ |  | CH₃ | Mix | Colorless Powder | 6.74–7.28(m, 12H), 5.95–6.12(m, 2H), 5.65(brs, 2H), 5.46(s, 1H), 5.40(s, 1H), 4.12–4.24(m, 2H), 3.58(s, 3H), 2.39(s, 3H), 2.35(s, 3H), 2.32(s, 3H), 2.31(s, 3H), 1.41(d, 3H), 1.33(d, 3H), 1.92–2.23(m, 4H) |
| 88 | 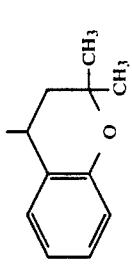 | CH₃ | CH₃ |  | CH₃ | Mix | Colorless Powder | 6.54–7.21(m, 14H), 5.94–6.04(m, 2H), 5.84(brs, 2H), 5.26(s, 1H), 5.19(s, 1H), 3.59(s, 3H), 3.57(s, 3H), 2.37(s, 3H), 2.33(s, 3H), 2.32(s, 3H), 2.30(s, 3H), 1.81–2.27(m, 4H), 1.45(s, 3H), 1.34(s, 6H), 1.30(s, 3H) |
| 89 | " | CH₃ | CH₃ | 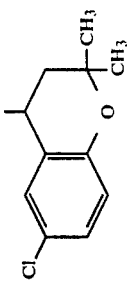 | CH₃ | Mix | Colorless Powder | 6.46–7.17(m, 12H), 5.79–5.97(m, 2H), 5.80(brs, 2H), 5.28(s, 1H), 5.16(s, 1H), 3.61(s, 3H), 3.57(s, 3H), 2.39(s, 3H), 2.35(s, 3H), 2.34(s, 3H), 2.31(s, 3H), 1.76–2.21(m, 4H), 1.46(s, 3H), 1.33(s, 6H), 1.28(s, 3H) |
| 90 | " | CH₃ | CH₃ | " | iPr | Mix | Colorless Powder | 6.47–7.22(m, 12H), 5.90–5.95(m, 2H), 5.73(brs, 2H), 5.23(s, 1H), 5.16(s, 1H), 4.88–4.97(m, 2H), 2.38(s, 3H), 2.35(s, 3H), 2.34(s, 3H), 2.32(s, 3H), 1.75–2.20(m, 4H), 1.47(s, 3H), 1.34(s, 3H), 1.33(s, 3H), 1.30(s, 3H), 1.17–2.24(m, 6H), 0.99–1.05(m, 6H) |
| 91 | " | CH₃ | CH₃ |  | CH₃ | Mix | Colorless Powder | 6.69–7.32(m, 14H), 5.90(m, 2H), 5.69(brs, 2H), 5.20(s, 1H), 5.17(s, 1H), 4.04–4.30(m, 4H), 3.58(s, 3H), 3.57(s, 3H), 2.35(s, 3H), 2.34(s, 2H), 2.30(s, 6H), 1.82–2.26(m, 4H) |
| 92 | " | CH₃ | CH₃ | " | CH₃ | A | Colorless Crystal mp 184–186° C. | 6.84–7.32(m, 7H), 5.90–5.91(m, 1H), 5.66(brs, 1H), 5.20(s, 1H), 4.04–4.22(m, 2H), 3.58(s, 3H), 2.34(s, 3H), 2.30(s, 3H), 2.02–2.12(m, 1H), 1.84–1.90(m, 1H) |
| 93 | 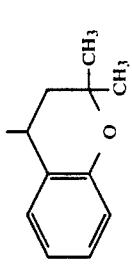 | CH₃ | CH₃ | " | CH₃ | Mix | Colorless Powder | 6.67–7.23(m, 16H), 5.94–6.06(m, 2H), 5.73(brs, 2H), 5.03(s, 1H), 4.98(s, 1H), 3.63(s, 3H), 3.62(s, 3H), 2.40(s, 3H), 2.37(s, 3H), 2.33(s, H), 1.79–2.27(m, 4H), 1.43(s, 3H), 1.35(s, 3H), 1.32(s, 3H) |

TABLE 8-continued

| Compound No. | X | R2 | R3 | Y | R1 | Steric type | Properties | NMR (CDCl3) δ ppm |
|---|---|---|---|---|---|---|---|---|
| 94 | 3,5-difluorophenyl | CH3 | CH3 | 2-(2-methyl-2-methoxypropyl)phenyl | CH3 | Mix | Colorless Powder | 6.54–7.28(m, 14H), 5.97–6.07(m, 2H), 5.79(brs, 2H), 5.03(s, 1H), 4.97(s, 1H), 3.65(s, 3H), 3.64(s, 3H), 2.40(s,3H), 2.37(s, 3H), 2.34(s, 3H), 2.33(s, 3H), 1.82–2.27(m, 4H), 1.43(s, 3H), 1.35(s, 3H), 1.33(s, 6H) |
| 95 | 2,6-difluorophenyl | CH3 | CH3 | 2-(2-methyl-2-methoxypropyl)-5-chlorophenyl | CH3 | Mix | Colorless Powder | 6.47–7.22(m, 12H), 5.73–5.95(m, 4H), 5.49(s, 1H), 5.37(s, 1H), 3.59(s, 3H), 3.56(s, 3H), 2.37(s, 3H), 2.23(s, 6H), 2.21(s, 3H), 1.73–2.21(m, 4H), 1.48(s, 3H), 1.34(s, 6H), 1.26(s, 3H) |
| 96 | benzofurazan-4-yl | CH3 | CH3 | chroman-4-yl | CH3 | Mix | Yellow Powder | 6.65–7.65(m, 14H), 5.96–5.98(m, 2H), 5.87–5.88(m, 2H), 5.41(s, 1H), 5.39(s, 1H), 3.91–4.32(m, 4H), 3.57(s, 3H), 3.54(s, 3H), 2.38(s, 3H), 2.36(s, 3H), 2.33(s, 3H), 2.31(s, 3H), 1.76–2.15(m, 4H) |
| 97 | " | CH3 | CH3 | 2-(2-methyl-2-methoxypropyl)phenyl | CH3 | Mix | Yellow Powder | 6.51–7.64(m, 14H), 5.92–6.06(m, 4H), 5.48(s, 1H), 5.40(s, 1H), 3.59(s, 3H), 3.55(s, 3H), 2.39(s, 3H), 2.34(s, 3H), 2.33(s, 3H), 2.31(s, 3H), 1.74–2.26(m, 4H), 1.46(s, 3H), 1.36(s, 3H), 1.29(s, 6H) |
| 98 | furan-2-yl | CH3 | CH3 | 2-(2-methyl-2-methoxypropyl)-5-chlorophenyl | CH3 | Mix | Colorless Powder | 6.20–7.33(m, H), 5.96–6.07(m, 2H), 5.87–5.89(m, 2H), 5.79–5.80(m, 2H), 5.22(s, 1H), 5.14(s, 1H), 3.68(s, 3H), 3.67(s, 3H), 2.40(s, 3H), 2.38(s, 3H), 2.35(s, 6H), 1.88–2.29(m, 4H), 1.43(s, 3H), 1.37(s, 3H), 1.36(s, 3H), 1.35(s, 3H) |
| 99 | thiophen-3-yl | CH3 | CH3 | 2-(2-methyl-2-methoxypropyl)phenyl | CH3 | Mix | Colorless Powder | 6.72–7.25(m, 12H), 5.90–6.02(m, 2H), 5.84(brs, 2H), 5.15(s, 1H), 5.09(s, 1H), 3.69(s, 3H), 3.66(s, 3H), 2.39(s, 3H), 2.38(s, 3H), 2.32(s, 3H), 2.31(s, 3H), 1.74–2.28(m, 4H), 1.42(s, 3H), 1.34(s, 3H), 1.31(s, 6H) |
| 100 | 3-nitrophenyl | NH2 | CH3 | chroman-4-yl | CH3 | Mix | Yellow Powder | 6.67–8.03(m, 16H), 6.50(brs, 2H), 6.19(brs, 4H), 5.88–5.90(m, 2H), 4.93(s, 3H), 4.90(s, 3H), 3.88–4.25(m, 4H), 3.58(s, 3H), 3.57(s, 3H), 2.35(s, 3H), 2.33(s, 3H), 1.80–2.15(m, 4H) |

TABLE 8-continued

| Compound No. | X | R$_2$ | R$_3$ | Y | R$_1$ | Steric type | Properties | NMR (CDCl$_3$) δ ppm |
|---|---|---|---|---|---|---|---|---|
| 101 | " | NH$_2$ | CH$_3$ | " | CH$_3$ | A | Yellow Crystal mp 140-143° C. | 6.85-8.04(m, 8H), 6.10(brs, 2H), 5.80-5.94(m, 2H), 4.93(s, 1H), 3.89-4.22 (m, 2H), 3.59(s, 3H), 2.36(s, 3H), 2.01-2.14(m, 1H), 1.78-1.88(m, 1H) |
| 102 | " | NH$_2$ | CH$_3$ | " | CH$_3$ | B | Yellow Powder | 6.67-7.90(m, 8H), 6.07-6.10(m, 3H), 5.87(m, 1H), 4.90(s, 1H), 4.22-4.35(m, 2H), 3.58(s, 3H), 2.38(s, 3H), 2.04-2.21(m, 2H) |
| 103 | " | NH$_2$ | CH$_3$ | (2-hydroxy-2-methylpropyl phenyl ether) | CH$_3$ | Mix | Yellow Powder | 6.78-8.08(m, 16H), 6.12(brs, 6H), 5.95-6.05(m, 2H), 5.02(s, 1H), 4.95(s, 1H), 3.60(s, 3H), 3.59(s, 3H), 2.41(s, 3H), 2.37(s, 3H), 1.79-2.26(m, 4H), 1.31(s, 6H), 1.30(s, 6H) |
| 104 | " | NH$_2$ | CH$_3$ | (chroman) | iPr | Mix | Yellow Powder | 6.78-8.08(m, 16H), 6.17(brs, 2H), 6.12(brs, 4H), 5.95-6.00(m, 2H), 5.09(s, 1H), 4.93(s, 1H), 4.89-4.91(m, 2H), 2.40(s, 3H), 2.36(s, 3H), 1.75-2.24(m, 4H), 1.47(s, 3H), 1.37(s, 3H), 1.32(s, 6H), 1.22-1.26(m, 6H), 1.00-1.04(m, 6H) |
| 105 | " | NH$_2$ | CH$_3$ | (chroman) | iPr | Mix | Yellow Powder | 6.65-8.05(m, 16H), 6.10(m, 6H), 5.86-5.90(m, 2H), 4.80-4.92(m, 4H), 3.89-4.32(m, 4H), 2.36(s, 3H), 2.34(s, 3H), 2.08-2.20(m, 4H), 1.22-1.27(m, 6H), 0.97-1.02(m, 3H), 0.86-0.88(m, 3H) |
| 106 | (dichlorophenyl) | NH$_2$ | CH$_3$ | " | CH$_3$ | Mix | Colorless Powder | 6.67-7.21(m, 14H), 6.18(brs, 2H), 6.09(brs, 4H), 5.87-5.88(m, 2H), 5.25-5.26 (m, 2H), 3.80-4.28(m, 4H), 3.53(s, 6H), 2.28(s, 6H), 1.83-2.20(m, 4H) |
| 107 | " | NH$_2$ | CH$_3$ | " | iPr | Mix | Colorless Powder | 6.38-7.26(m, 14H), 6.16(brs, 4H), 5.87-5.91(m, 2H), 5.24(s, 1H), 5.23(s, 1H), 4.87-4.92(m, 2H), 4.11-4.25(m, 4H), 2.22(s, 3H), 2.21(s, 3H), 1.98-2.08(m, 4H), 1.19-1.30(m, 6H), 0.88-0.92(m, 6H) |
| 108 | " | NH$_2$ | CH$_3$ | (2-hydroxy-2-methylpropyl phenyl ether) | CH$_3$ | Mix | Colorless Powder | 6.74-7.23(m, 14H), 6.28(brs, 2H), 6.13(brs, 4H), 5.94-6.04(m, 2H), 5.33(s, 1H), 5.28(s, 1H), 3.544(s, 3H), 3.538(s, 3H), 2.30(s, 3H), 2.26(s, 3H), 1.90-2.20(m, 4H), 1.42(s, 3H), 1.31(s, 3H), 1.30(s, 3H), 1.27(s, 3H) |
| 109 | " | NH$_2$ | CH$_3$ | " | iPr | Mix | Colorless Powder | 6.50-7.26(m, 14H), 6.30(brs, 2H), 6.16(brs, 4H), 5.99-6.01(m, 2H), 5.32(s, 1H), 5.27(s, 1H), 4.89-4.93(m, 2H), 2.26(s, 3H), 2.23(s, 3H), 1.92-2.20(m, 4H), 1.41(s, 3H), 1.31(s, 3H), 1.20-1.28(m, 9H), 0.90-0.93(m, 3H) |

TABLE 8-continued

| Compound No. | X | R₂ | R₃ | Y | R₁ | Steric type | Properties | NMR (CDCl₃) δ ppm |
|---|---|---|---|---|---|---|---|---|
| 110 | 3-CN-phenyl | NH₂ | CH₃ | chroman-4-yl | CH₃ | Mix | Colorless Powder | 6.78–7.48(m, 16H), 6.35(brs, 2H), 6.13(brs, 4H), 5.87(m, 2H), 4.83(s, 2H), 3.82–4.32(m, 4H), 3.59(s, 3H), 3.57(s, 3H), 2.34(s, 6H), 1.88–2.11(m, 4H) |
| 111 | " | NH₂ | CH₃ | " | iPr | Mix | Colorless Powder | 6.78–7.47(m, 16H), 6.60(brs, 2H), 6.18(brs, 4H), 4.86–4.90(m, 2H), 4.82(s, 1H), 4.81(s, 1H), 3.84–4.32(m, 4H), 2.30(s, 3H), 2.29(s, 3H), 1.82–2.20(m, 4H), 1.21–1.29(m, 6H), 0.97–1.02(m, 6H) |
| 112 | 3-CN-phenyl | NH₂ | CH₃ | 2,2-dimethylchroman-4-yl | CH₃ | Mix | Colorless Powder | 6.72–7.52(m, 16H), 6.50(brs, 2H), 6.16(brs, 4H), 5.95–6.04(m, 2H), 4.93(s, 1H), 4.87(s, 1H), 3.60(s, 3H), 3.58(s, 3H), 2.36(s, 3H), 2.34(s, 3H), 1.92–2.28(m, 4H), 1.44(s, 3H), 1.36(s, 3H), 1.30(s, 6H) |
| 113 | " | NH₂ | CH₃ | " | iPr | Mix | Colorless Powder | 6.57–7.52(m, 16H), 6.18(brs, 4H), 5.94–6.00(m, 2H), 4.86–4.92(m, 2H), 2.36(s, 3H), 2.33(s, 3H), 1.70–2.28(m, 4H), 1.46(s, 3H), 1.36(s, 3H), 1.19–1.31(m, 9H), 0.85–1.05(m, 3H) |
| 114 | benzo[c][1,2,5]oxadiazol-4-yl | NH₂ | CH₃ | chroman-4-yl | CH₃ | Mix | Yellow Powder | 6.66–7.63(m, 14H), 6.30(brs, 2H), 6.07(brs, 4H), 5.87(m, 2H), 5.25(m, 2H), 3.90–4.34(m, 4H), 3.55(s, 3H), 3.52(s, 3H), 2.33(s, 3H), 2.31(s, 3H), 1.76–2.16(m, 4H) |
| 115 | " | NH₂ | CH₃ | " | iPr | Mix | Yellow Powder | 6.65–7.62(m, 14H), 6.37(brs, 2H), 6.10(brs, 4H), 5.82–5.94(m, 2H), 5.24(m, 2H), 4.80–4.92(m, 2H), 3.92–4.34(m, 4H), 2.31(s, 3H), 2.28(s, 3H), 1.82–2.20(m, 4H), 1.23(s, 3H), 1.20(s, 3H), 0.86–0.94(m, 12H) |
| 116 | " | NH₂ | CH₃ | 2,2-dimethylchroman-4-yl | CH₃ | Mix | Yellow Powder | 6.52–7.65(m, 14H), 6.35–6.42(m, 2H), 6.10(brs, 4H), 5.94–6.01(m, 2H), 5.32(s, 1H), 5.24(s, 1H), 3.57(s, 3H), 3.53(s, 3H), 2.36(s, 3H), 2.31(s, 3H), 1.46(s, 3H), 1.34(s, 3H), 1.29(s, 6H) |
| 117 | " | NH₂ | CH₃ | " | iPr | Mix | Yellow Powder | 6.52–7.65(m, 14H), 6.40–6.47(m, 2H), 6.13(brs, 4H), 5.94–6.01(m, 2H), 5.32(s, 1H), 5.25(s, 1H), 4.83–5.04(m, 2H), 2.35(s, 3H), 2.31(s, 3H), 1.74–2.15(m, 4H), 1.49(s, 3H), 1.36(s, 3H), 1.30(s, 6H), 1.21–1.26(m, 6H), 0.90–0.98(m, 6H) |

What is claimed is:

1. A dihydrodropyridine derivative represented by the following formula (I)

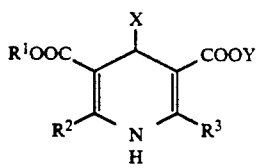

wherein $R^1$ represents a lower alkyl group; a lower alkyl group substituted by substituents selected from the group consisting of lower alkoxy, lower cycloalkyl, N-methyl-N-benzylamino, and cyano; a lower alkenyl group; or a 3,4-dihydro-2H-benzo[b]pyran-4-yl group $R^1$ and $R^3$, which may or may not be the same, independently represent a lower alkyl group or an amino group X represents a phenyl group substituted by one or more substituents selected from the group consisting of halogen, lower alkyl, lower alkoxy, halo-lower alkyl, halo-lower alkoxy, nitro, and cyano; and a naphthyl group Y represents a 3,4-dihydro-2H-benzo[b]pyran-4-yl group; a 3,4-dihydro-2H-benzo[b]pyran-4-yl group substituted by one or more substituents selected form the group consisting of lower alkyl, lower alkoxy, halogen, and cyano; or a salt thereof, with the proviso that when $R^1$ and Y are the same, X is a nitro substituted phenyl group.

2. A therapeutic agent having antihypertensive action comprising an effective amount of dihydropyridine compound or salt thereof according to claim 1 and a pharmaceutically acceptable carrier.

3. A method for lowering blood pressure comprising administering a therapeutically effective amount of a dihydropyridine compound or salt thereof according to claim 1 to a host.

* * * * *

UNITED STATES PATENT AND TRADEMARK OFFICE
CERTIFICATE OF CORRECTION

PATENT NO. : 5,260,444

DATED : NOVEMBER 9, 1993

INVENTOR(S) : TERUKAGE HIRATA ET AL

It is certified that error appears in the above-indentified patent and that said Letters Patent is hereby corrected as shown below:

Column 1, line 1, "DIHYDROPYRIDINE DERIVATIVE" should read --NOVEL DIHYDROPYRIDINE DERIVATIVE--.

Column 5, line 4, "pyran-4-yi group" should read --pyran-4-yl group--.

line 32, "S-nitro" should read --5-nitro--.

Column 16, Compound No. 13, "6.83-7.33(m, 16H)," should read --6.82-7.33(m, 16H),--

Column 21, Compound No. 26, "4.96(s, 3H)," should read --4.96(s, 1H),--.

Column 33, line 24, "J=13.SHz)," should read --J=13.5Hz--

Column 50, Compound No. 109, "6.50-7.26(m, 14H)," should read --6.50-7.24(m, 14H),--.

UNITED STATES PATENT AND TRADEMARK OFFICE
CERTIFICATE OF CORRECTION

PATENT NO. : 5,260,444
DATED : NOVEMBER 9, 1993
INVENTOR(S) : TERUKAGE HIRATA ET AL

It is certified that error appears in the above-indentified patent and that said Letters Patent is hereby corrected as shown below:

Column 53, line 19, "$R^1$ and $R^3$" should read --$R^2$ and $R^3$--.

Column 54, line 9, "form the group" should read --from the group--.

Signed and Sealed this

Seventh Day of February, 1995

Attest:

BRUCE LEHMAN

Attesting Officer

Commissioner of Patents and Trademarks